(12) United States Patent
Degani et al.

(10) Patent No.: US 9,480,599 B2
(45) Date of Patent: Nov. 1, 2016

(54) DEVICE AND METHOD FOR LASER ASSISTED DEEP SCLERECTOMY

(75) Inventors: Joshua Degani, Jerusalem (IL); Ami Eyal, Maccabim-Reut (IL)

(73) Assignee: I Optima Ltd., Ramat Gan (IL)

( * ) Notice: Subject to any disclaimer, the term of this patent is extended or adjusted under 35 U.S.C. 154(b) by 1525 days.

(21) Appl. No.: 13/142,803

(22) PCT Filed: Dec. 31, 2009

(86) PCT No.: PCT/IL2009/001238
§ 371 (c)(1),
(2), (4) Date: Sep. 26, 2011

(87) PCT Pub. No.: WO2010/076799
PCT Pub. Date: Jul. 8, 2010

(65) Prior Publication Data
US 2012/0116372 A1    May 10, 2012

Related U.S. Application Data

(60) Provisional application No. 61/202,184, filed on Feb. 4, 2009, provisional application No. 61/193,865, filed on Dec. 31, 2008.

(51) Int. Cl.
*A61F 9/011* (2006.01)
*A61F 9/008* (2006.01)
*A61B 3/13* (2006.01)

(52) U.S. Cl.
CPC ............... *A61F 9/008* (2013.01); *A61B 3/13* (2013.01); *A61F 2009/00865* (2013.01)

(58) Field of Classification Search
CPC ..................... A61F 9/008; A61F 2009/00872
USPC ........................................................ 606/4, 5
See application file for complete search history.

(56) References Cited

U.S. PATENT DOCUMENTS

| 6,241,721 B1 | 6/2001 | Cozean et al. |
| 6,258,082 B1 | 7/2001 | Lin |
| 2002/0013573 A1* | 1/2002 | Telfair .................. A61B 3/113 606/5 |
| 2005/0096639 A1* | 5/2005 | Slatkine .............. A61F 9/00802 606/5 |

FOREIGN PATENT DOCUMENTS

| EP | 0 770 370 A2 | 5/1997 |
| WO | WO 90/09141 A2 | 8/1990 |
| WO | WO 03/041623 A1 | 5/2003 |

* cited by examiner

*Primary Examiner* — William Thomson
*Assistant Examiner* — Jeffrey Lipitz
(74) *Attorney, Agent, or Firm* — Greenberg Traurig LLP

(57) ABSTRACT

An ophthalmic laser ablation system is described with various optional features, some especially suitable for non-penetrating filtration on an eye. In one example, focusing of an ablation laser uses a movable lens coupled to a pair of converging light sources, which converge at the focal distance of the lens. In another example, laser ablation settings are selected for optimal ablation and minimal amount of thermal damage of a layer of percolating scleral tissue.

8 Claims, 17 Drawing Sheets

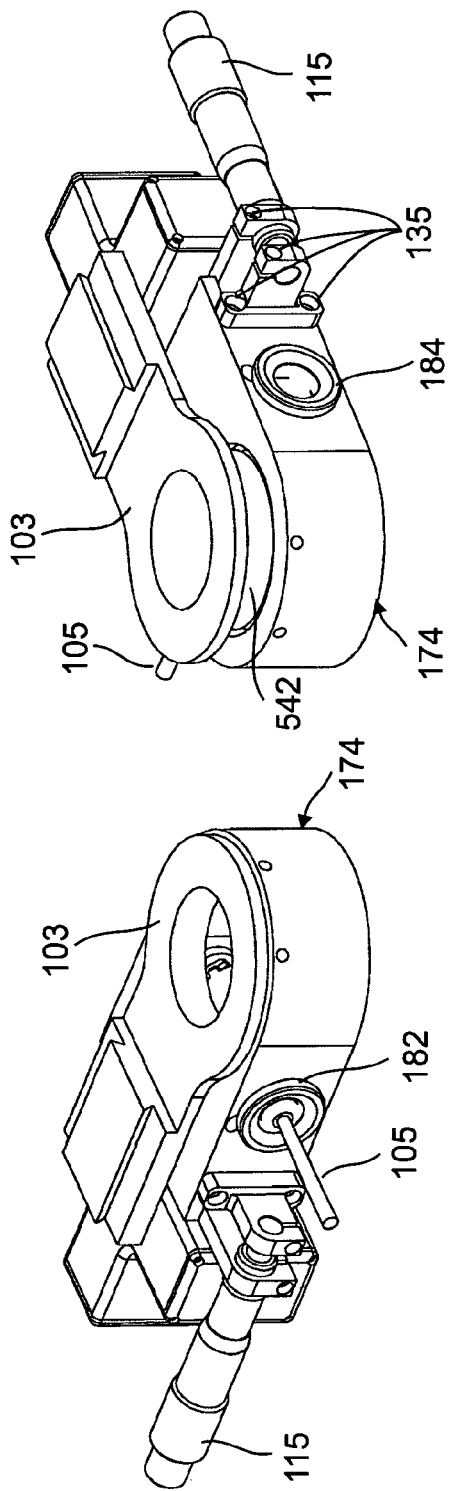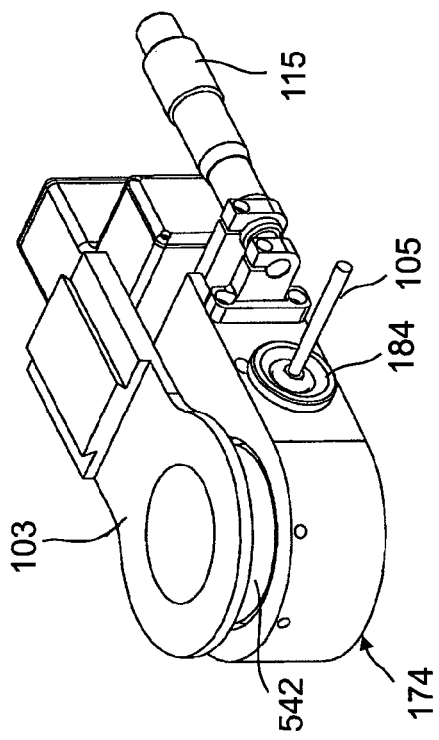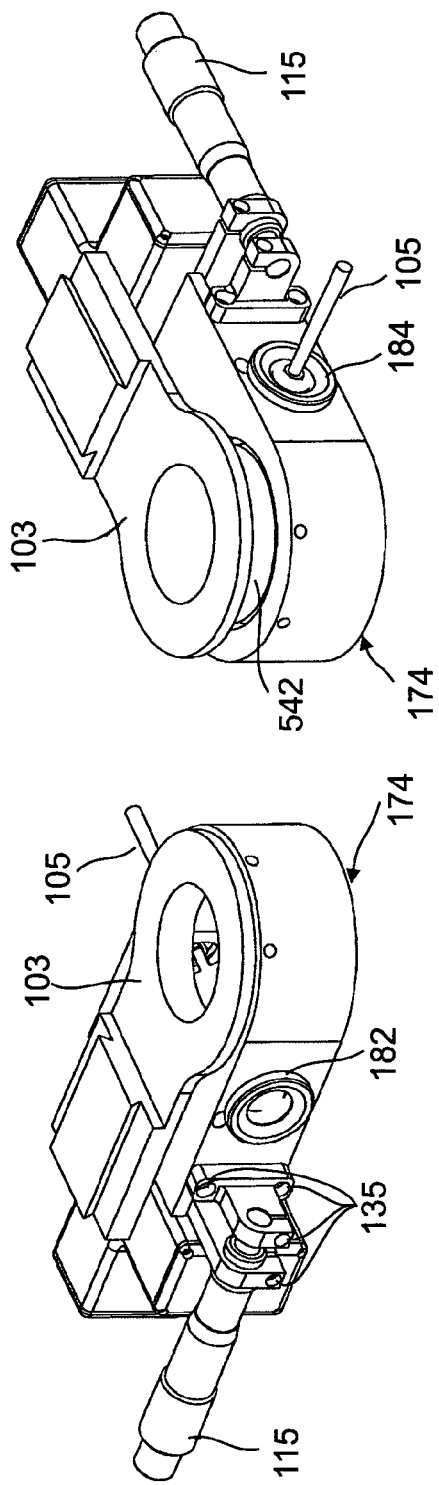

Table-2

Table 3

DEVICE AND METHOD FOR LASER ASSISTED DEEP SCLERECTOMY

RELATED APPLICATION

This application is corresponds to PCT/IL2009/001238, filed Dec. 31, 2009, which claims the benefit under 35 USC 119(e) of U.S. Provisional Patent Application No. 61/193,865, filed Dec. 31, 2008, and U.S. Provisional Patent Application No. 61/202,184, filed Feb. 4, 2009, the disclosures of which are incorporated herein by reference in their entirety.

FIELD OF THE INVENTION

The present invention, in some embodiments thereof, relates to methods and systems for ameliorating raised inter ocular pressure, and more particularly but not exclusively to a laser ablation system for non-penetrating sclerectomy.

BACKGROUND

Glaucoma is a group of diseases, frequently characterized by raised intraocular pressure (IOP), which affects the optic nerve, and is the second leading cause of blindness in the world. Currently, most glaucoma patients are initially managed with medical therapy. However, some patients still require surgical interventions to preserve their vision. When glaucoma continues to progress despite the use of medication regimes and possibly laser treatments (ALT or SLT treatments), a glaucoma filtration procedure (trabeculectomy) may be recommended. Additional surgical techniques for reducing intraocular pressure (IOP) include laser trabeculoplasty, non-penetrating filtration surgery (i.e. deep sclerectomy, viscocanalostomy), shunts, and cyclo-destructive procedures.

Deep sclerectomy, a non-penetrating or minimally invasive filtering surgery, is being proposed as a viable alternative to conventional trabeculectomy. In contrast to trabeculectomy, which is associated with significant morbidity, deep sclerectomy does not penetrate the eye, and has been shown to minimize intraoperative and postoperative complications.

In a manual non-penetrating deep sclerectomy (NPDS) procedure performed with manual surgical instruments, a deep scleral flap is first dissected and then a second scleral layer is cut out, leaving an exposed thin layer of trabecular meshwork and Descemet's membrane. Fluid percolation through the remaining tissue is the desired outcome of the procedure. Inadvertent perforation of the thin trabeculodescemet membrane or alternatively an insufficiently deep second scleral flap, are relatively frequent complications, occurring in about 30% of the cases in the early stages of the learning curve of this procedure. In the case of perforation, the procedure may be converted to a conventional trabeculectomy; however, the high rates of perforation and a long learning curve limit the use of deep sclerectomy as a common treatment procedure. While the risk of perforation is relatively high, if the tissue is not cut deep enough, the filtration may not be effective and the intraocular pressure will not be reduced to the desired level. Since the scleral tissue needs to be dissected to more than 90% of its depth, leaving a residual intact layer of only several tens of microns, the procedure is very demanding and requires significant skills and expertise.

The following publications may be relevant to this application:

RE 37504 of U.S. Pat. No. 5,549,598

| | | |
|---|---|---|
| U.S. Pat. No. 3,828,788 | | |
| U.S. Pat. No. 4,665,913 | May 1987 | L'Esperance, Jr. |
| U.S. Pat. No. 4,907,586 | March 1990 | Bille et al. |
| U.S. Pat. No. 4,963,142 | October 1990 | Loertscher |
| U.S. Pat. No. 5,098,426 | March 1992 | Sklar et al. |
| U.S. Pat. No. 5,364,390 | November 1994 | Taboada et al. |
| U.S. Pat. No. 5,370,641 | December 1994 | O'Donnell, Jr. |
| U.S. Pat. No. 5,520,679 | May 1996 | Lin |
| U.S. Pat. No. 5,529,076 | June 1996 | Schachar |
| U.S. Pat. No. 5,620,435 | April 1997 | Belkin et al. |
| U.S. Pat. No. 5,634,920 | June 1997 | Hohla |
| U.S. Pat. No. 5,733,276 | March 1998 | Belkin |
| U.S. Pat. No. 5,738,677 | April 1998 | Colvard et al. |
| U.S. Pat. No. 5,782,822 | July 1998 | Telfair et al. |
| U.S. Pat. No. 5,827,266 | October 1998 | Harel et al. |
| U.S. Pat. No. 6,010,497 | January 2000 | Tang et al. |
| U.S. Pat. No. 6,059,772 | May 2000 | Hsia et al. |
| U.S. Pat. No. 6,159,202 | December 2000 | Sumiya et al. |
| U.S. Pat. No. 6,220,247 | April 2001 | Maldonado Bas |
| U.S. Pat. No. 6,241,721 | June 2001 | Cozean et al. |
| U.S. Pat. No. 6,258,082 | July 2001 | Lin |
| U.S. Pat. No. 6,263,879 | July 2001 | Lin |
| U.S. Pat. No. 6,540,391 | April 2003 | Lanzetta et al. |
| U.S. Pat. No. 7,135,016 | | |
| US 2001/0029363 | October 2001 | Lin |
| US 2002/0026179 | February 2002 | Toh |
| US 2005/0096639 | | |
| EP 0 765 648 | April 1997 | |
| EP 0 770 370 | May 1997 | |
| EP 1 138 290 | October 2001 | |
| WO 01/50969 | July 2001 | |
| WO 01/085044 | | |
| WO 03/041623 | | |

Assia E. I. et al. Experimental studies on non-penetrating filtration surgery using the CO2 laser. Graefes Arch Clin Exp Ophthalmol. 2007 June; 245(6):847-54

Barak, A. et al; "Anterior Capsulotomy Using CO2 Laser;" SPIE; vol. 3246; pp. 196-198; June 1998.

Assia, E. I. et al.; "Non-Penetrating Glaucoma Surgery Using the CO$_2$ Laser: Experimental Studies in Human Cadaver Eyes;" Proceedings of SPIE; vol. 4245; pp. 228-233; June 2001.

Belkin, M. et al.; "Non-Penetrating Trabeculectomy Using the CO$_2$ Laser in Rabbits;" Abstract No. 1419-B327; IOVS; vol. 40; No. 4; Mar. 15, 1999. Wolbarsht, M.; "Laser Surgery: CO$_2$ or HF;" IEEE Journal of Quantum Electronics; vol. QE-20; No. 12; pp. 1427-1432; December 1984.

SUMMARY OF THE INVENTION

The present invention discloses a laser ablation control system. The systems comprises a frame adapted for attachment to an ophthalmic microscope and including a portion adjacent to the field of view of the microscope; a beam combiner adjacent to the portion and in the field of view of the microscope; a beam scanner adjacent to the portion and with an output directed toward the beam combiner; and, a converging lens between the scanner and the beam combiner.

It is according to one embodiment of the invention wherein the aforesaid system further comprises at least one member chosen from the group consisting of: (i) at least one of (a) an input for a carbon dioxide laser; and, (b) a carbon dioxide laser; (ii) a displacer adapted to control the distance between the lens and the beam combiner; (iii) adapting means for coupling the frame to a microscope; (iv) at least two light sources positioned adjacent to the lens and coupled thereto, disposed such that light output from the light sources is directed toward the beam combiner, and configured to have a predetermined spacing of light spots generated thereby at the focal length of the lens; (v) a frame's protrusions-based mechanism useful to mount the system on an ophthalmic microscope, wherein the frame of the system further comprises at least protrusions as follows: (a) a first protrusion adapted to extend from the frame towards the field of view and to contact the adapter; (b) a second, adjustable, protrusion adapted to be combined with the first protrusion and prevent removal of the frame from the adapter; and (c) a third, adjustable, protrusion adapted to lock the frame to the adapter; (vi) at least one patterned light source fixedly coupled to the lens disposed such that light output from the patterned light source is directed the beam combiner, and adapted to generate a pattern having a predetermined form at a focal location of the output; and, (vii) a focus adjusting element adapted to move the lens in tandem with the patterned light source to change the distance of the lens from plane of operation (i.e., the patient's eye).

It is according to another embodiment of the invention wherein at least one of the following is true: (a) a focus of the scanned beam is at a distance of more than about 130 mm from the beam combiner; and (b) the depth of field of the scanned beam is between about 2 and about 8 mm. The term 'about' is defined hereinafter as ±20% of the defined measure.

It is according to another embodiment of the invention wherein the aforesaid system additionally comprises at least one patterned light source. This light source characterized by at least one of the group consisting of: (i) a pattern comprising at least two point sources, generating a converging pair of rays that converge at the focal location; (ii) a pattern comprising at least two point sources each of which is mounted between about 3 and about 7 cm, especially 5 cm from the center of the lens and on opposite sides thereof; and, (iii) a pattern comprising at least two point sources each of which is mounted between about 2 and about 5 cm, especially 3 cm from the center of the lens.

It is according to another embodiment of the invention wherein at least one of the following is true: a. the beam combiner comprises a path folding mirror configured to be transparent to most wavelengths of visible light and configured to reflect both ablation wavelengths and the patterned light; b. the frame is adapted to rotate relative to the microscope; c. the beam combiner is positioned at a side of the field of view of the beam scanner; d. the system further comprises a micromanipulator adapted for manual adjustment of the beam combiner; and e. the beam combiner comprises a path folding mirror configured to be fully reflective to all wavelengths.

It is also in the scope of the invention wherein another laser ablation control system is presented. This system comprises a. a card reader; b. a laser beam controller; and, c. circuitry configured to control one or both of the laser beam controller and a laser beam source in accordance with data read by the card reader to perform ablation suitable for non-penetrating filtration surgery on an eye.

It is according to one embodiment of the invention wherein in the aforesaid system at least one of the following is true: a. the circuitry is adapted to prevent firing of an ablation laser by the laser beam controller; b. the circuitry is adapted to prevent scanning of an ablation laser by the laser beam controller; c. the circuitry is adapted to limit the time of activation i.e., the time during which the controller is active of the controller; d. the circuitry is adapted to limit the number of activations of the laser beam controller or the laser beam source; and, e. the circuitry is adapted to control the controller by transmitting to the controller ablation parameters suitable to ablate a thickness of scleral tissue, according to the data.

It is also in the scope of the invention wherein another laser ablation control system is presented. This system comprises a. a laser beam controller; b. a device chosen from the group consisting of (a) a manual triggering mechanism for triggering the controller and (b) a laser source; and, c. circuitry chosen from the group consisting of (a) circuitry configured to prevent triggering of the controller within a repeat delay time of at least 0.5 seconds from the previous triggering and (b) circuitry configured to drive the controller with parameters suitable for removal of scleral tissue in a thickness of at least 10 microns and for avoidance of thermal damage within a thickness of more than 30 microns, in a layer of percolating scleral tissue.

It is according to one embodiment of the invention wherein in the aforesaid system at least one of the following is true: a. the removal is by thermal vaporization; b. the parameters cause thermal damage of at least 50 microns in thickness in an upper layer of scleral tissue; c. the ratio between thickness of thermal damage between the percolating layer and the upper layer is at least 1:5; d. the thickness beyond which damage is avoided is less than 20 microns in thickness; and e. the circuitry is also configured to drive the controller with parameters which cause thermal damage in a thickness of at least 30 microns in the layer of percolating scleral tissue.

It is according to another embodiment of the invention wherein this system further comprises a linear displacement element adapted to modify a distance between the lens and the beam combiner in a plane generally perpendicular to a line of sight of the field of view.

It is also in the scope of the invention wherein another laser ablation control system is presented. This system is adapted for mounting on an ophthalmic microscope, and comprises a laser scanner which scans light in two dimensions, and further wherein the components of the laser ablation control system comprise a plurality of modules configured for modular rearrangement.

It is according to another embodiment of the invention wherein in the aforesaid system at least of the following is true: a. the system is adapted for rearrangement in an operating room; b. at least one of the modules is adapted for reversal with respect to another module; c. at least one of the modules is adapted for attachment to a plurality of multiple locations on another of the modules; and d. at least two of the modules are configured to couple a light beam between the modules in an alignment set by mechanical coupling thereof.

It is also in the scope of the invention wherein another laser ablation control system is presented. This system comprises (a) a frame adapted for attachment to an ophthalmic microscope and including a portion which is adjacent to a field of view of the microscope; (b) a beam combiner in the field of view of the microscope; (c) a beam scanner with an output directed toward the beam combiner; (d) a manipulator configured to adjust the beam combiner; and, (e) a focus controlling element adapted to modify the distance between the frame and a focal point of the output.

Each of the manipulator and the focus controlling element has at least two possible mounting points on the frame.

It is also in the scope of the invention wherein a system for mounting on an ophthalmic microscope is presented.

This system comprises (a) an adapter ring adapted to be fixedly attached to an ophthalmic microscope and comprising a ring adapted to be located in a field of view of the microscope; (b) a frame adapted to be mounted on the adapter ring; and, (c) at least three protrusions on the frame, directed towards the ring, comprising: (i) a first protrusion extending from the frame towards the field of view and in physical contact with the adapter; (ii) a second, adjustable, protrusion adapted to be combined with the first protrusion and to prevent removal of the frame from the adapter; and (iii) a third, adjustable, protrusion adapted to lock the frame to the adapter.

It is also in the scope of the invention wherein a method of indicating focusing of ablating laser is presented. The method comprises steps of a. providing a laser beam suitable for ablating tissue; b. focusing the laser beam by using a converging lens; and c. aiming a plurality of beams from the lens and adjusting the beams to converge at the focal length.

It is according to one embodiment of the invention wherein this method further comprises step of folding the laser beam and the plurality of beams using a one mirror.

It is also in the scope of the invention wherein a method of ablating scleral tissue in order to achieve percolation is presented. This method comprises steps of a. providing a laser; b. setting laser application to predefined parameters so as to provide minimal thermally damaged tissue at a percolation layer above one or both of a Schlemm canal and a trabecular meshwork of the eye; and c. activating the laser according to the parameters to achieve the percolation, by ablating scleral tissue overlying the percolation layer.

It is according to one embodiment of the invention wherein the aforesaid method further comprises a step of applying to the area of scleral tissue ablated an amount of at least one material chosen from the group consisting of anti-inflammatory materials and anti-proliferation materials sufficient to reduce scarring.

It is also in the scope of the invention wherein a method of laser ablation of scleral tissue is presented. This method comprises steps of a. targeting a laser at a first area overlying a Schlemm canal and/or a trabecular meshwork; b. targeting the laser at a second area with an overlap of at least about 25% with the first area; c. targeting the laser at a third area in a direction substantially perpendicular to a line connecting the first and the second areas, with an overlap of at least about 25% with the first area; and d. repeating steps (a) to (c) until percolation sufficient to reduce intra-ocular pressure in all three of the areas is achieved.

It is according to one embodiment of the invention wherein the aforesaid method comprises at least one step chosen from the group consisting of: a. providing an overlap of at least about 30% between the first area and the second area and of at least about 30% between the second area and the third area; and b. targeting the laser by scanning, such that a condition chosen from the group consisting of (i) the overlaps are uniform in substantially all of the scan or (ii) at least two of the overlaps are not equal in substantially all of the scan is true.

It is further in the scope of the invention wherein a method of laser ablation of scleral tissue is presented. This method comprises steps of (a) defining a target region for a laser as including a concave portion following the outer curvature of a limbus; and, (b) scanning a laser along the region, until percolation sufficient to reduce intra-ocular pressure is achieved in the target region.

It is according to one embodiment of the invention wherein the step of defining a target region for a laser is provided by including a region at least about 2 mm long and at least about 0.5 mm wide along a curvature of a limbus and within a range of between about 0.2 and about 1.6 mm from the outer curvature of a limbus; and further wherein the step of scanning a laser along the region is performed until percolation sufficient to reduce intra-ocular pressure is achieved from the target region.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A-6D illustrate various configurations of a BMS, in accordance with an exemplary embodiment of the invention;

DESCRIPTION OF EXEMPLARY EMBODIMENTS OF THE INVENTION

Figure 1:
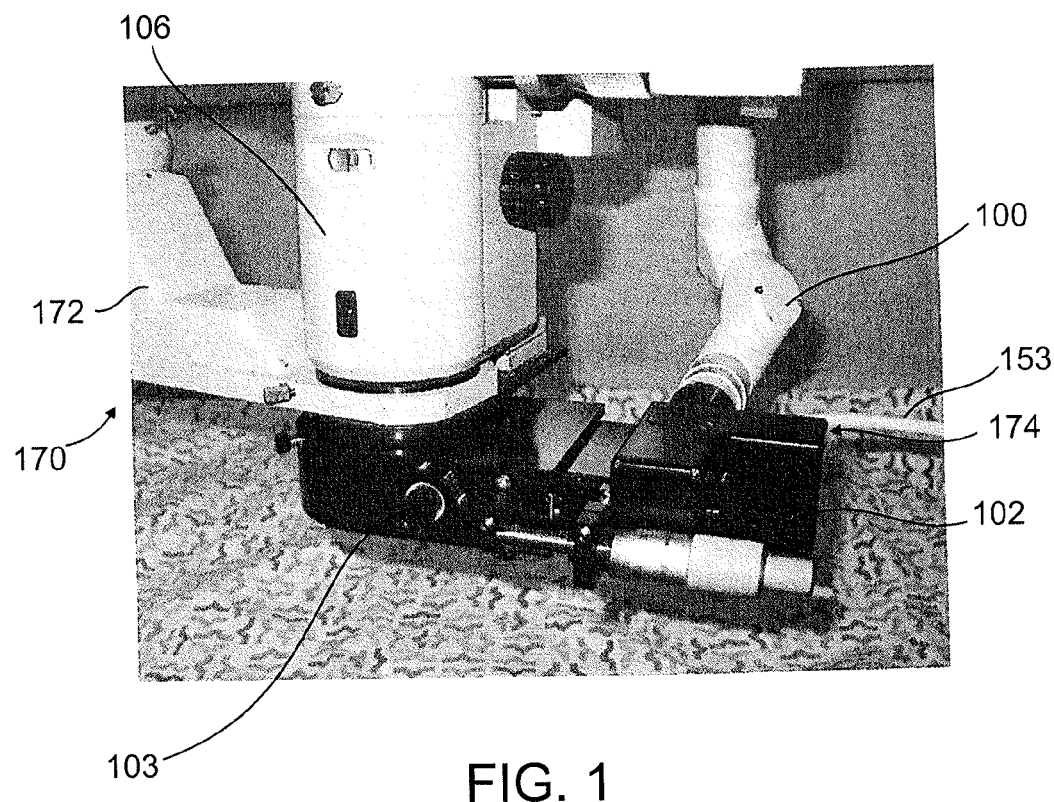
FIG. 1 is a picture of a beam manipulation system (BMS) mounted on an ophthalmic microscope (OM) and connected to a laser source using an articulated arm, in accordance with an exemplary embodiment of the invention.

The present invention, in some embodiments thereof relates to methods and apparatus for treating high intra ocular pressure, using laser ablation, and in particular, but not limited to, scanning regimes, laser parameters, optical design, post-operative treatment, reduction of scarring, aiming methods and/or eye protection.

An aspect of some embodiments of the invention relates to ease of use of a laser ablation system in accordance with exemplary embodiments of the invention. In an exemplary embodiment of the invention, a distance between the system (e.g., a scanning ablation source and a microscope) and the eye is at least 10, 15, 20 or more centimeters. Optionally, this distance allows a physician to place his hands between the microscope/scanner and an eye, without touching the microscope and/or maximizes the available free space as dictated by the optics of the ophthalmic microscope. In an exemplary embodiment of the invention, such distance is provided by providing a beam combiner for reflecting laser light from a source thereof at an entrance of said laser light into a field of view of the microscope. It should be noted that such design may be more complex than providing the combining at a far side of the field of view, as if the beam combiner is adjustable, such design may cause mechanical interference between an adjustment mechanism for adjusting the beam combiner and the laser source. In an exemplary embodiment of the invention, separation is provided by changing the focal length of a lens focusing the ablation laser. Optionally, however, the lens focal length is selected to match the microscope focal length.

In an exemplary embodiment of the invention, adjustment of the beam combiner is used to precisely locate the ablation region on the eye. Optionally, for example as described below, adjustment includes translation (in one or two dimensions) and rotation. Optionally, an aiming beam is used to indicate a location where a flap is to be cut. This may allow the entire procedure to be under the guidance of the system.

Optionally or alternatively, the optics of the laser source are set up so that a significant depth of field of operation is provided, for example, 3, 4, 5, 6 or more mm. In an exemplary embodiment of the invention, such depth of field is provided by using a low-diopter focusing lens for the laser source (optionally more than one lens is used). Optionally, the laser source is a CO2 laser. Other lasers may be used, but this may affect the desired dwell times and/or spot sizes. For example, a laser which removes less tissue at a given time period may be provided with a shorter dwell time or an increased number of automatic repetitions, so that a desired thickness (e.g., 5-50 microns) is removed. In some cases, the spot size and dwell time or laser pulse time are determined by the type of laser-tissue interaction (e.g., required energy density).

Optionally or alternatively, the position of the operational field relative to the microscope is moved using a micrometer and without moving the ablation system portions that are mounted on the microscope (e.g., the scanner and/or beam combiner are not moved relative to the microscope). In an exemplary embodiment of the invention, the scanner is moved and the beam combiner and optional micromanipulator are not moved. This may allow repositioning when the microscope head with the system on it and/or the patient are moved for any reason during a procedure or between procedures. In an exemplary embodiment of the invention, the micrometer moves a focusing lens of the scanned laser beam towards or away from the microscope and a beam-combining reflecting mirror, thereby the micrometer changes the optical distance between the laser source and the eye being treated. In some embodiments, for example, as noted above, the lens is moved with the scanner.

In an exemplary embodiment of the invention, the repositioning of the operational field (and/or its width) of the laser is carried out to provide and/or maintain an alignment between the optics of the laser and the optics of the microscope. This may allow better monitoring of the tissue being ablated, as the focal planes of the laser (ablation) and the microscope (monitoring) would be aligned.

In an exemplary embodiment of the invention, the beam combining mirror can be adjusted manually (e.g., act as a micromanipulator).

Optionally or alternatively, a focus aiming system with a pattern is provided, which pattern indicates if the treated surface of the eye is within the operational depth of field. In an exemplary embodiment of the invention, the focus aiming system comprises a plurality of separate visible laser sources, which are aimed to converge and/or cross and optionally do not share the focusing optics of the ablation source. Rather, the sources are designed to converge/cross and/or be within a known (optionally small) distance from each other, at the operational field. In an exemplary embodiment of the invention, the combining mirror is sized and made of materials suitable to reflect the focus aiming beams as well, while minimizing interference with the microscope. Optionally, each focus aiming laser has a focusing lens having a focal length similar to that of the focusing lens of the ablation laser (e.g., to the point of expected convergence of the two beams). In an exemplary embodiment of the invention, the focal length of the focus laser(s) is adjusted to converge on the tissue—according to its location in the designed system. Optionally, such focusing lenses serves to improve accuracy of the focusing sub-assembly In an alternative embodiment the two lasers share the lens with the ablation laser, albeit, this may depend on the wavelength involved and available space.

Optionally or alternatively, an aiming beam for indicating the ablation location and/or flap formation location is coaxial with the ablation laser beam and shares a significant part of the optical path thereof. Such an aiming beam may be scanned with the ablation laser, for example if it is optionally combined with the ablation laser beam before scanning, rather than after scanning.

An aspect of some embodiments of the invention relates to reducing scarring and/or thermal damage (which may promote scarring). It has been surprisingly been discovered by the inventors that laser settings which cause significant thermal damage when ablating scleral tissue, can be selected to cause substantially no or very reduced thermal damage (e.g., over at least 70%, 80%, 90% of the area) at a layer of scleral tissue adjacent the Schlemm canal and/or trabecular meshwork. Optionally, the parameters of ablation are modified as the ablation depth increases and approaches the level of the Schlemm canal. Alternatively, the ablation parameters are selected to be optimal for the areas adjacent percolation. In an exemplary embodiment of the invention, the ablation parameters, including, for example, overlap between adjacent ablated areas, power and/or dwell time are selected so as to make use of the thermal mass provided by percolating fluid. Optionally, thermally damaged tissue is ablated and new tissue not damaged, as the percolating layer is reached, with heat being transported by the percolating fluid, which can serve as a very large heat sink. Optionally or alternatively, the laser layer of scleral tissue is not thermally damaged as it is protected by such a thermal sink and/or percolating fluid. Optionally, the time delay until a same location is ablated is set so that such a protected layer can be protected by new percolation. Optionally, such percolation is seen by an operator (and/or an automated system) and used as a signal to stopping the procedure.

In an exemplary embodiment of the invention, scleral tissue is assumed to vary in that it has different thermal relaxation times (TRT). Thus, for example, to reduce thermal damage for a lower TRT tissue, higher source power, shorter dwell times and/or smaller spot sizes may be needed. Optionally, however, tissue which is or near at a percolation layer, includes a significant percentage of water, providing, for example, a larger thermal sink (e.g., possibly also in adjacent tissue) and/or a longer thermal relaxation time, thus allowing a longer dwell time and possibly a lower power density to achieve a desired amount of thermal damage. Using such settings at a higher scleral layer might cause significant thermal damage, due to the dwell time being longer than the TRT of the higher layer. In an exemplary embodiment of the invention, the laser parameters are matched to the TRT of the tissue to be ablated and/or to other properties thereof, such as thermal capacity and evaporation point and/or material disassociation point. Optionally, the matching is to tissue which is at least 70%, 80%, 90% or intermediate percentages by volume of water.

In an exemplary embodiment of the invention, thermal damage thickness at the lowest layer of the sclera is less than 50 micron, 40 micron, 30 microns, 20 microns or 10 microns (over most of said area, for example, over 80% thereof), optionally being invisible. Optionally or alternatively, the ratio between thermal damage thickness at the lowest layer and at the highest layer is a factor of at least ×2, ×4, ×6, ×10 or intermediate factor. Optionally, the system is preconfigured with laser ablation settings optimized for minimal damage at the lowest scleral layer, even if such settings cause considerable damage at higher layers. Optionally or alternatively, the system is programmed also with laser parameters suitable for minimizing and/or reducing thermal damage to upper layers of the sclera. This may be useful, for example, to ensure that if a two step ablation procedure is performed, with some of the sclera ablated to percolation and some not, that there is reduced damaged tissue which may cause scarring.

In some embodiments of the invention, a certain, measured amount of thermal damage and/or leftover char material is desired, as a means of preventing adhesions and/or preventing full healing (either of which may reduce percolation) and/or otherwise preventing of percolation reduction. Optionally, this amount is, for example, between 5 and 50 microns thick, for example, between 10 and 30 microns thick.

In an exemplary embodiment of the invention, adjacent laser ablation targets are selected to overlap by, for example, 10%, 20%, 30%, 40% or more, of the diameter of the focused beam (e.g., for uniformly shaped targets, the distance between target centers is for example, 30% less the target extent in the direction connecting the two target centers). In an exemplary embodiment of the invention, the overlap is provided in two orthogonal directions. Optionally, the overlap is not uniform, for example, being greater or smaller as the ablation process approaches/overlies the Schlemm's canal. In some cases, overlap between adjacent scan lines (and time between consecutive and/or overlapping ablations) is also taken into account when determining the energy deposition per time unit as being enough to ablate before heat leaks away (e.g., to adjacent tissues), and/or not being too high.

Overlap may be useful to compensate for a non-uniform power cross-section of the beam. Typically, beam intensity is Gaussian in cross-section (though other non-uniform patterns may be used as well), meaning that the edges of the target may receive less power than the center. Overlapping can correct this imbalance of power deposition. In some embodiments, the beam cross-section is selected so that a circular beam with suitable overlap can provide substantially uniform energy deposition (e.g., within a factor of 2 or 3).

In an exemplary embodiment of the invention, the ablation parameters, including overlap are selected so that areas with too high an overlap factor are not overly thermally damaged, while areas with no overlap or possibly no direct beam contact, if any, receive enough energy from adjacent target areas, to be ablated. Optionally, the overlap is selected so that border regions of a target receive enough energy (e.g., from two or more targeting events), to overcome any heat loss due to conduction, which loss might prevent proper ablation.

In an exemplary embodiment of the invention, additional parameters are varied, for example, dwell time is reduced, for example, to 300-500 microseconds (e.g., 320) and pulse power is increased, for example to between 18 and 50 watts (e.g., 24). Optionally, this keeps the deposited energy the same, and may allow the dwell time to be shortened, possibly below thermal relaxation tine. Other dwell times, for example, between 1 microsecond and 300 microsecond (possibly suitable for short pulse lasers) or between 500 and 1000 microsecond, may be used. By dwell time is meant the amount of time that the laser is aimed at the tissue in a certain location, even if the power output of the laser (on the tissue) is low or zero at the time. Tissue interaction time is typically shorter for pulsed and/or shuttered lasers, and is the sub-portion of time during which the laser is aimed at the tissue and powered.

In an exemplary embodiment of the invention, the dwell time or ablation repetition time is made longer (or shorter) than a tissue thermal relaxation time, according to the desired effect. Optionally, the relaxation time in soft tissues is taken to be between 0.5 and 0.7 or 1 milliseconds and the dwell time and/or tissue interaction time and/or time between repeated pulses to a same location is made shorter thereof.

In an exemplary embodiment of the invention, a parameter that is selected is the laser wavelength and/or laser type. Optionally, this is by replacing the laser and/or tuning a tunable laser. Optionally or alternatively, laser parameters are changed so as to change the laser-tissue interaction, for example, selecting between vaporization, vaporization and then tissue particles ejection by the pressure of the vaporized tissue, molecular disassociation, photo-disruption, and other non-thermal photo-ablation of tissue. It should be noted that changing laser often changes the amount of tissue removal for each ablation, which may be compensated for by automated repeated ablation at a same point a predetermined number of times, calculated to achieve a desired removal amount in a removal step.

In an exemplary embodiment of the invention, the beam is made rectangular, optionally to promote more uniformity in overlap.

In an exemplary embodiment of the invention, when using laser ablation, for example, as described herein, scarring is reduced and/or procedure success increased by needling, a processes wherein a needle or other thin sharp object is placed in the ablation crater and moved around to disengage any adhesions which may have formed with the flap.

Optionally or alternatively to needling, pressure is temporarily reduced in the eye, using a goniopuncturing of the eye. Such pressure reduction and/or needling is optionally applied after the ablation procedure is completed, for example, after a few days (e.g., 2-5 days), weeks (e.g., 1-4) or months (e.g., 2-10), possibly after 1 or more years.

In an exemplary embodiment of the invention, needling and/or goniopuncturing is applied when percolation is slowed down, for example, due to adhesions and/or other adverse physiological conditions. Such puncturing should be distinguished from penetration into the eye, often characterized by a large hole and/or tear which is large enough cause iris prolapse.

Optionally or alternatively, the ablated area is treated with anti-inflammatory materials, steroid and/or non-steroid.

Optionally or alternatively, the ablated area is treated with anti-proliferation materials.

Optionally, the space between the ablated area and the flap is filled with a spacer/implant, optionally biodegradable, viscoelastic material such as Healon5, which optionally dissipates after a while (e.g., 5-20 days, 1-3 weeks or 2-3 months or year). Alternatively, the spacer and/or material stays in the eye indefinitely.

Optionally or alternatively to treatment immediately after the ablation, treatment is continued for several days or weeks thereafter.

In an exemplary embodiment of the invention, pressure-reducing drugs are stopped after a few days or weeks. Optionally or alternatively, intra-ocular pressure goes down to below-pathological levels.

Some such methods may also be applied to non-laser non-penetrating filtration surgery.

An aspect of some embodiments of the invention relates to scan parameters. In an exemplary embodiment of the invention, the scan shape is defined to include a concave section, optionally selected to match a curvature of a limbus of the eye. In an exemplary embodiment of the invention, this scan path is chosen so as to ensure ablation over the Schlemm canal, which is found within 0.2-1.6 mm from the limbus. Optionally or alternatively, the scan path (e.g., and the ablation region) is otherwise shaped to include some or all of the region distanced between about 0.2 and 1.6 mm from the limbus, along the scleral tissue layer.

It should be noted that the position of the limbus changes as a function of the depth into the sclera. Optionally, the positioning of the ablation region is changed based on the actual thickness of flap that is cut (e.g., thereby determining the limbus position).

In an exemplary embodiment of the invention, the scan is carried out using curved movements of the beam, for example, movements along lines that are parallel to the concave section. Optionally, the part of the scan distal from the limbus is convex. Optionally or alternatively, the scan path is using straight raster lines. Optionally or alternatively, the distal part of the scan is straight, rather than concave.

In an exemplary embodiment of the invention, the scans overlap, optionally with a uniform overlap.

In an exemplary embodiment of the invention, a two step scanning process is used. In a first step, an entire region is scanned, for example, about 3 by 6 mm. Then, note is taken of where some percolation is found. Optionally, this indicates the position of the Schlemm's canal buried within the Sclera layer. A second ablation step is carried out only in the area, or in a fixed scan shape including the area, where there is percolation.

In an exemplary embodiment of the invention, an ablation area is subdivided into sub-areas, each one being ablated separately, possibly to a different depth.

In an exemplary embodiment of the invention, the flap which is prepared before the ablation is considerably larger than the planned first (and/or second) ablation areas, for example, being 1-2 mm larger in extent in 1, 2, 3, or 4 cardinal direction compared to the ablation area. The flap may have up a large circumferential length (e.g., parallel to the limbus—of 5, 6 or 7 mm). Optionally, the longer the length the better in terms of having large percolation area.

In an exemplary embodiment of the invention, controlling software and/or circuitry of the ablation system is set up to include two ablation pattern sizes, optionally with different ablation parameters (e.g., with different optimizations for thermal damage). Optionally, the system is provided with a control, for example, a button, which determines which size and/or other, optionally predetermined, settings are used. Optionally, the button has only two settings. Alternatively, additional settings are provided, such as 3 or 4. Optionally, the control is a foot-pedal or is adjacent or mounted on the micromanipulator controls.

An aspect of some embodiments of the invention relates to an eye protector (e.g., for protecting corneal/scleral tissue and/or internal tissues such as a retina). In an exemplary embodiment of the invention, the eye protector is mounted on the cornea and/or also beyond it and includes a window (e.g., or a notch) for passing the ablation laser and aiming light wavelengths at the region of the flap. Optionally or alternatively, outside of the window, the ablation light and, optionally; the aiming light are blocked (e.g., 90%, 95%, 98% or 99.9% blockage) by the protector. In an exemplary embodiment of the invention, the protector is a high-water content gel, for example, with more than 40% water content. Alternatively or additionally, other materials which absorb the specific laser radiation, even if they have no water content, may be used. Optionally, a material is chosen which does not emit toxic and/or hot particles or fluids when hit by the ablation laser. Optionally, the protector is a contact lens with an aperture or other shape (e.g., depression or optics-affecting treatment) formed therein. Optionally, the protector is shaped to cover the cornea and/or includes extensions radially extending on either side of the planned ablation area to prevent inadvertent ablation outside the planned region.

In an exemplary embodiment of the invention, the protector is designed (e.g., thickness) to properly function for only a small number of ablations, for example, 1, 2, 3 or between 4 and 10 ablation acts, or the number of ablation acts allowed or expected in a procedure.

In an exemplary embodiment of the invention, the protector is transparent to visible light or at least to parts of the visible spectrum substantially everywhere, so a physician can view the eye through it.

In an exemplary embodiment of the invention, the protector is opaque to visible light or at least to parts of the visible spectrum, optionally substantially for its entirety, so the visible laser cannot pass through it.

An aspect of some embodiments of the invention relates to ease of mounting of the laser ablator on an ophthalmic microscope. In an exemplary embodiment of the invention, an adaptor is provided to fix the ablator to a microscope. Optionally, the adapter attaches to the microscope using standard methods (e.g., screws at standard locations).

In an exemplary embodiment of the invention, the ablator is coupled to the adapter with two types of mountings, a first type for providing coupling but optionally allowing rotation of the ablation system around the optical axis of the field of view, and a second one for providing rigidity. Optionally, rotation is used to align the ablation shape with an actual flap formation location.

In an exemplary embodiment of the invention, trans-axial (to microscope axis) alignment is provided using a hierarchy of connection methods. In an exemplary embodiment of the invention, an aperture of the ablator mounts on a ring of the adapter, which is itself aligned with the microscope. In an exemplary embodiment of the invention, a plurality of screws extend into said aperture and against said ring. Optionally, first plurality of screws (or fixed protrusions) define two points of a triangle (or other geometry). A second plurality of screws (or single screw), optionally symmetric with respect to the axis of the triangle, may be used for ensuring that the ablator cannot fall off the adaptor, for example, if the adaptor ring has a lip (or a groove or one or more depressions) and the shape defined by the screws has a minimum diameter smaller than that of the lip (or matching the groove and/or depressions). A third screw or screws, optionally symmetric with respect to the shape, is used for fixing the aperture to the ablator, by friction, optionally retarding and/or preventing rotation thereof.

In an exemplary embodiment of the invention, the scanning system is provided as multiple (e.g., 2, 3, 4, 5, 6 or more) modular components which can optionally be easily (e.g., in an OR or other non-workshop setting, e.g., using a standard tool such as a screwdriver or hex wrench) rearranged for various mounting situations and/or have parts replaced for different situations. In one example, the adapter is a separate element which may be matched to a particular microscope design. In another example, a beam scanner and a beam combiner may be coupled in a plurality of manners to match geometrical considerations. Optionally, the beam combiner is designed to mount in both a normal position and a flipped position on a microscope/adapter, for example, by using a mirror which is reflected on both sides.

Optionally, at least two of the modules have their own separate housings. Optionally, at least one module can be reversed with respect to another module for attachment thereto. Optionally, at least two modules share this ability to be reversed in assembly.

In an exemplary embodiment of the invention, the scanning system is designed to include multiple positions for attaching one or more of user manipulation controls, for example, a beam combiner adjuster and field location adjustor. In an exemplary embodiment of the invention, such manipulation controls may be positioned in a location where their physical presence does not interfere with other tools in the operating space, while preserving their functionality.

An aspect of some embodiments of the invention relates to an enforced delayed (also termed herein "repeat delay") between repeated ablation of a same location. In an exemplary embodiment of the invention, the ablation procedure comprises repeated ablations, with each ablation removing, for example, 5-50 microns or some other desired amount. Optionally, initial ablations are thicker than later ablations or the system includes a button to select ablation depth. It should be noted that for some laser parameter settings and lasers, a desired ablation depth is achieved by repeated ablation of a same point. However, once such a desired ablation depth is achieved, it is generally desirable to visually inspect the eye (or some other means) to determine if percolation has started and/or is sufficient. In some cases, a user may inadvertently apply a second ablation before such checking and/or may not wait long enough to see the effects of ablation, to see percolation and/or to allow the self-limiting protective feature caused by percolation to come into action. In an exemplary embodiment of the invention, the ablation system enforces a minimal delay. In one example, the trigger mechanism includes electronics (e.g., a capacitor circuit) which does not accept a second pressing of the trigger if a desired delay (e.g., preset to 1-3 seconds or user settable) has not passed. Optionally or alternatively, such a delay is enforced using a mechanical means, for example, a slow return on the trigger to an "armed position" and/or by a safety being automatically engaged. Optionally or alternatively, such a delay is enforced using computer control, which measures time. Optionally, the delay is determined, at least in part on the number and/or position of ablation repetitions so far. Optionally or alternatively, the total number of ablations is limited, to prevent inadvertent damage to the eye (e.g., shock damage) which may be caused by continuous ablation of a percolation layer.

An aspect of some embodiments of the invention relates to control of the usage of the ablation system. In an exemplary embodiment of the invention, a card is provided which is precharged with usage parameters and optionally ablation parameters. Optionally, such a card is a smart card, a memory card, an RFID and/or a bar-code or other computer readable media. In an exemplary embodiment of the invention, the ablation system includes a suitable card reader. Optionally, the card includes the information encoded thereon. Optionally, the card is writable and can be written by the ablation system (e.g., using the reader). Optionally or alternatively, the card includes a code which is used to access the information, for example, information stored in the system or available by a network connection.

In an exemplary embodiment of the invention, the card includes thereon or links to one or more of:

(a) card ID;
(b) device ID;
(c) times at which devices are allowed to be or were (e.g., for a writable card) activated; and
(d) procedure parameters (e.g., one or more of laser parameters, number of ablation steps allowed (e.g., parameter being between 4 and 25 or 100), ablation thickness (e.g., between 5 and 75 microns), repeat delay (e.g., between 1 and 4 seconds), allowed pause (e.g., time after which it is assumed that a procedure was stopped, for example, a value between 3 and 7 minutes) and total procedure time (e.g., a value between 10 and 30 minutes)).

Optionally, a card is provided for one procedure. In other embodiments, a card supports multiple procedures.

In an exemplary embodiment of the invention, a procedure cannot be started without a card being read and/or being inserted in a reader. Optionally, the card controls the turning on of the laser and/or a shutter which allows passage of laser light to the scanner. In an exemplary embodiment of the invention, the time of the procedure is measured from when the ablation laser is turned on (e.g., via the system or manually and then sensed), or from a first or second ablation step. Optionally or alternatively, the scanner will not operate without the card. In an exemplary embodiment of the invention, an aiming beam is provided and does not count as part of the procedure time. When the allotted time is up or when the allowed number of ablation step performed, the card is deactivated and the procedure cannot continue. This can be used as a safety feature to avoid over ablation. Optionally, a safety feature is provided in that if a procedure is prematurely terminated due to card logic for some reason, removing and inserting the card (optionally only the same card) will allow an additional time span and series of shots. Optionally, this time is a loan and is recouped by canceling of the next inserted card without allowing a procedure to be performed.

Optionally, the cards are used to control billing, with each card being sold for a fixed sum and/or a particular device and/or procedure (e.g., a card scheme can also be used for other laser based procedures).

In an exemplary embodiment of the invention, a range of cards are provided. For example, a "factory card" can be used in an unlimited manner. A technician card may, for example, read form the device the past usage log and/or require changing of a site and/or device between reuses. A test card is optionally provided, for example, for daily or other testing of the system. Optionally, testing is on a blank, for example, Type "Classic Crest" made by Neenah Paper Inc. (Alpharetta, Ga., USA) In an exemplary embodiment of the invention, the test card causes the system to generate a pattern which is unsuitable for the desired procedure, for example, including a correctly shaped test area, with adjacent ablation areas, which, in a human eye would, for example, overlie the cornea. Optionally, the testing shows if a correct amount and shape of tissue will be ablated when the system is in use.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. In particular, various aspects and features of the invention may be practiced in conjunction with scleral ablation systems or other eye and/or laser treatment systems other than the OT-134 and OT-133 and variants thereof described in greater detail below.

Overview of OT-134 Embodiments

Referring now to the drawings, FIGS. 1-6D illustrate components, subcomponents and assemblies of a laser ablation control system (LACS), in accordance with an exemplary embodiment of the invention. Various features, options and alternatives are also discussed below. The system, adapted for mounting on an ophthalmic microscope or being made integral with one, generally comprises a source of a scanned laser beam and a beam combiner for combining with a line of sight of a microscope. In an exemplary embodiment of the invention, the scanned beam is focused. Optionally, an aiming pattern source is provided. Various adjustment and coupling mechanisms are optionally provided. It is a particular feature of some embodiments of the invention, that the LACS is distanced from the focal location of the laser beam by at least 130-170 mm, allowing for a physician to easily pass a hand between the eye and the LACS, without accidentally contaminating the LACS and/or moving it. It is a particular feature of some embodiments of the invention that the LACS can be easily adjusted so that the ablating laser beam is in focus on the target.

In addition, described below are various ablation parameters. It should be noted that such parameters may be applied with systems other than described herein.

OT-134 Beam Manipulating System—General Description

The LACS includes a Beam Manipulating System (BMS) and a controller (not shown), for example, a computer with a display, which controls the BMS. Optionally or alternatively, the BMS includes an onboard controlling circuit. In an exemplary embodiment of the invention, the controller is programmed for and/or accepts user input, to drive the BMS to perform various scan paths and/or dwell times. Optionally, the controller is programmed to prompt a user (e.g., using an audio, including optionally speech and/or a visual reminder) what is a next step to perform during a procedure. Optionally, also not shown, LACS includes a vision system (e.g., a camera and an image processor) which views the treated area and provided feedback, optionally automated, optionally to a user for example, on correct focusing of the laser and/or positioning with respect to the cornea or other landmark of the eye. Methods for identifying the cornea and/or visible laser beams are known in the art and may be used for this. Optionally, the vision system views through the microscope. Alternatively, the vision system is mounted (e.g., on the microscope or patient or bed), possibly without exact calibration, so long as it views the treated area. Optionally, such feedback may, but need not, include feedback on starting of percolation or of sustained functional percolation.

FIG. 1 shows a BMS 174 mounted in configuration 170 for use. The BMS is an opto-mechanical system which is used to ablate tissue in conjunction with a $CO_2$ laser and (optionally) a microscope 106 (an optional second viewer 172 is also shown). The BMS receives as input laser beam, optionally a static laser beam, for example one exiting from the articulated arm of a medical grade $CO_2$ laser system 100. In other embodiments, the controller also controls the laser source, for example, its power and/or intrinsic pulse or other temporal parameters.

Figure 2:
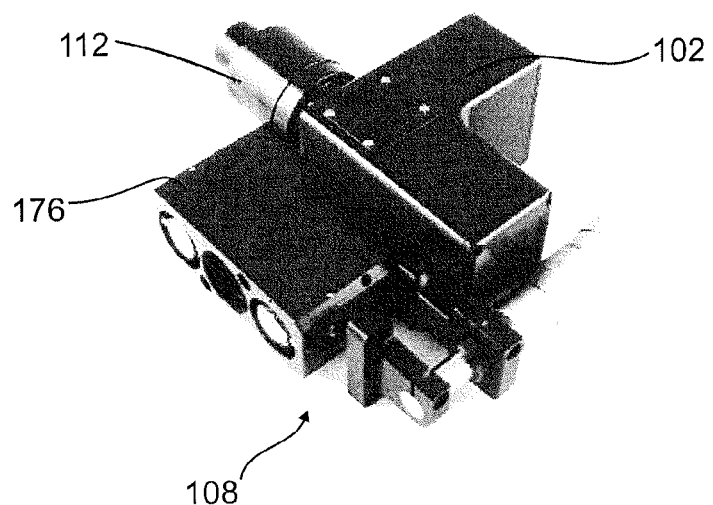
FIG. 2 is a picture of a beam scanning portion and focusing sub-system of the device of FIG. 1, in accordance with an exemplary embodiment of the invention.
Figure 3A:
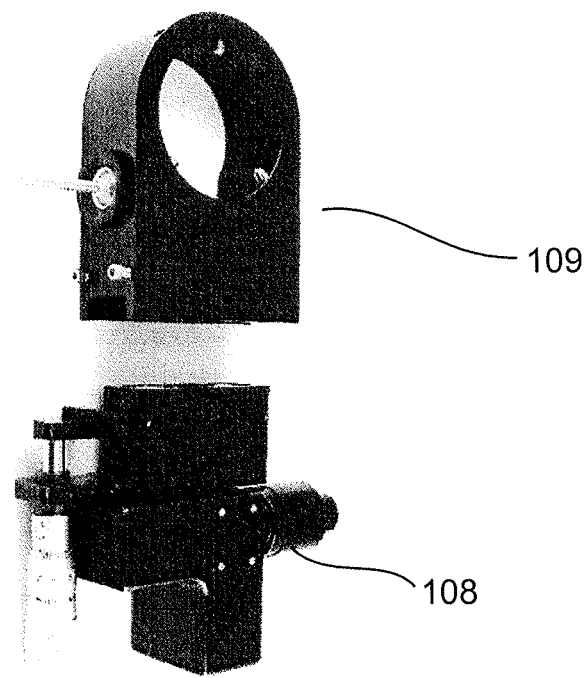
FIG. 3A and FIG. 3B illustrate the attachment of a beam combiner and micromanipulator together with the beam scanning portion of FIG. 2, with an optional focus controller, in accordance with an exemplary embodiment of the invention.
Figure 3B:
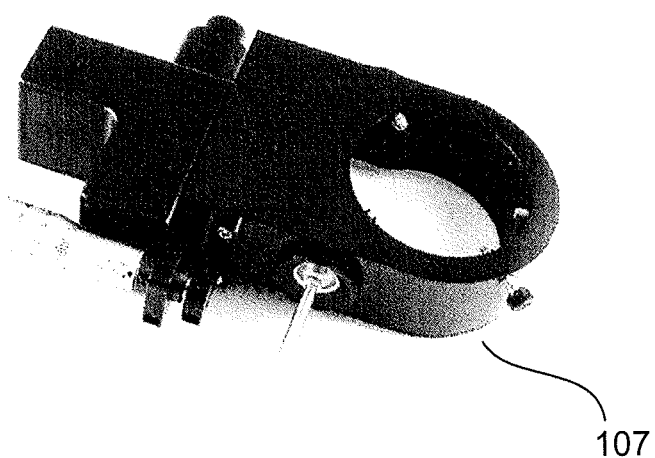
Figure 4A:
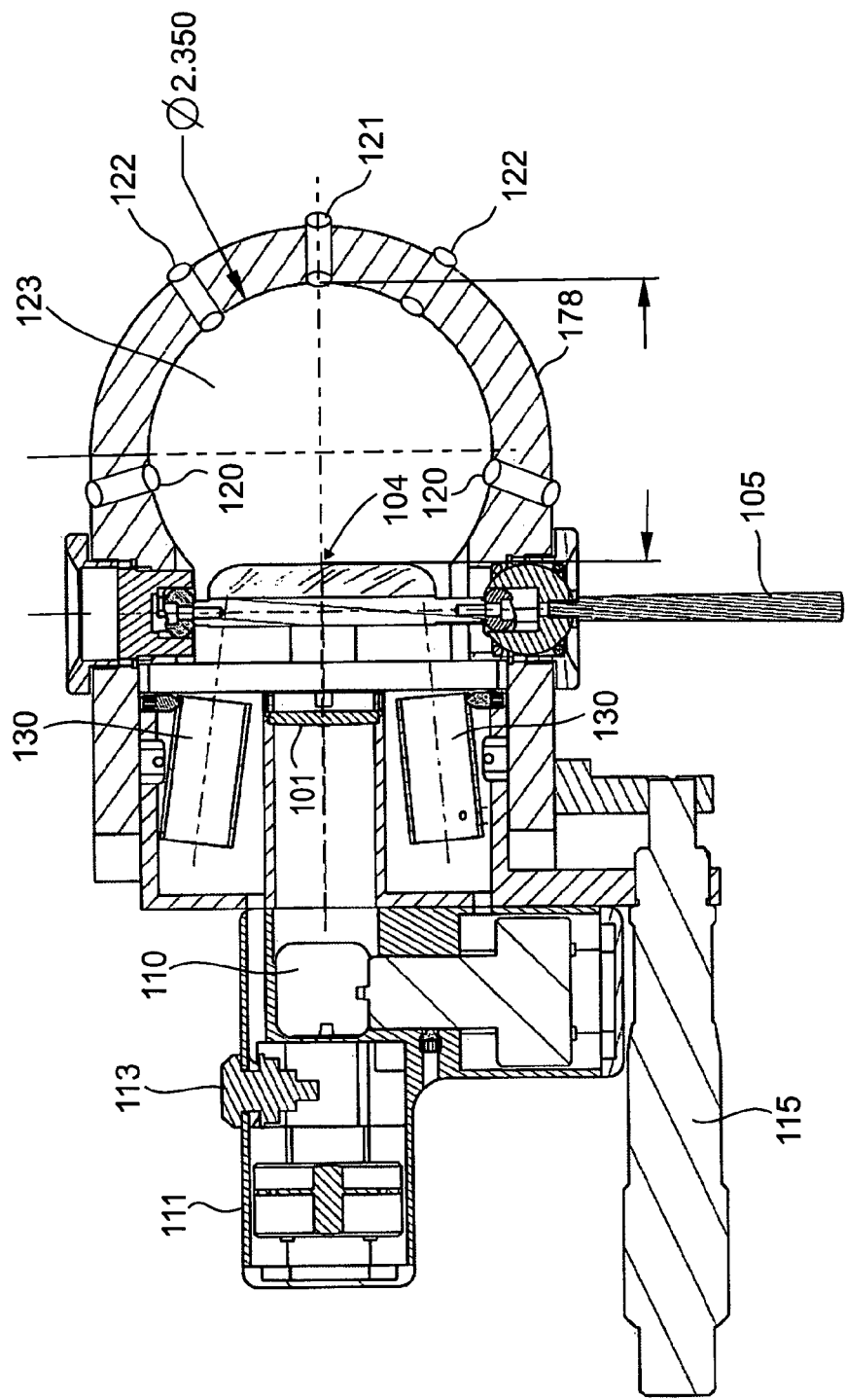
FIG. 4A is a cross-sectional view and FIG. 4B is an isometric view of the micromanipulator, the beam combiner and the beam scanner of FIG. 3, with FIG. 4B also showing an adapter, in accordance with an exemplary embodiment of the invention.
Figure 4B:
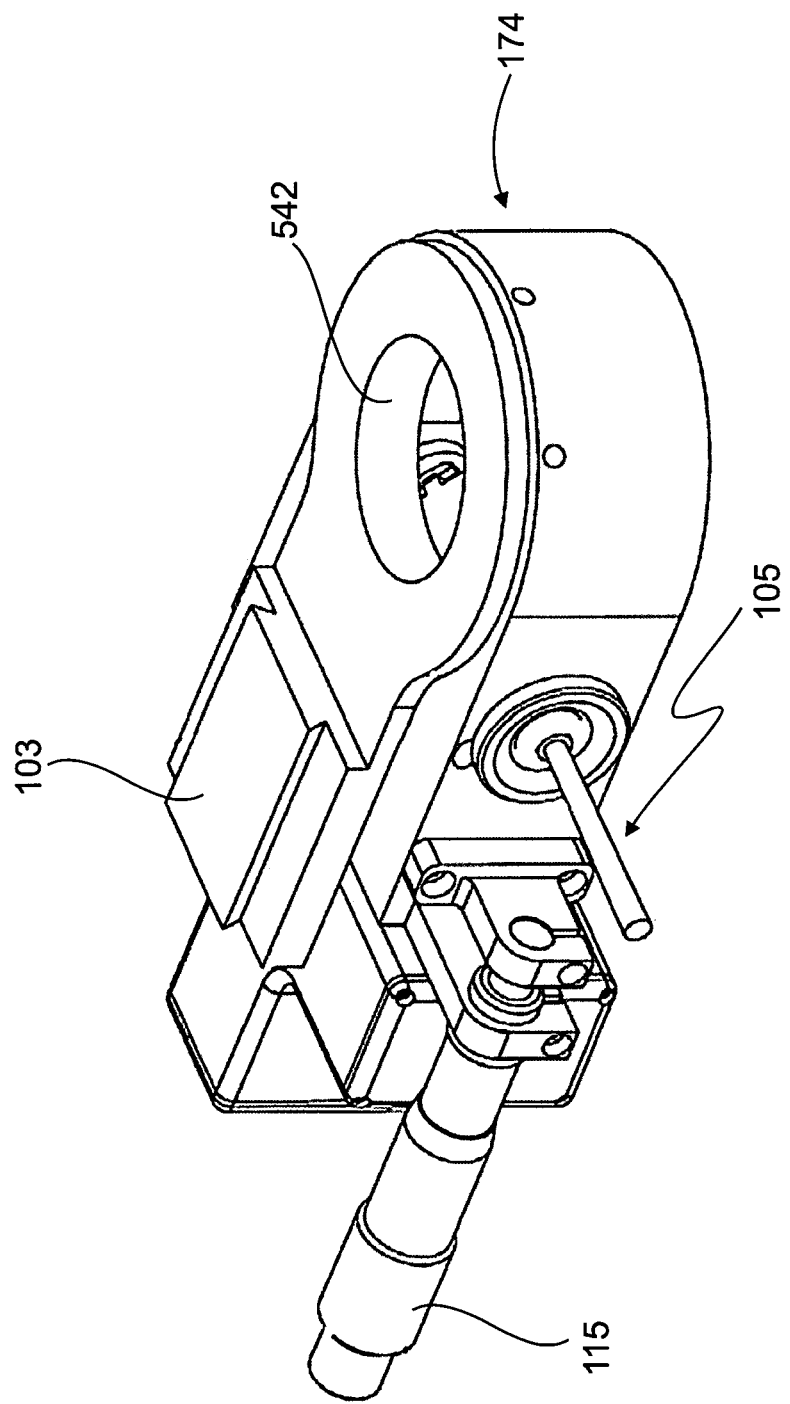
Figure 5:
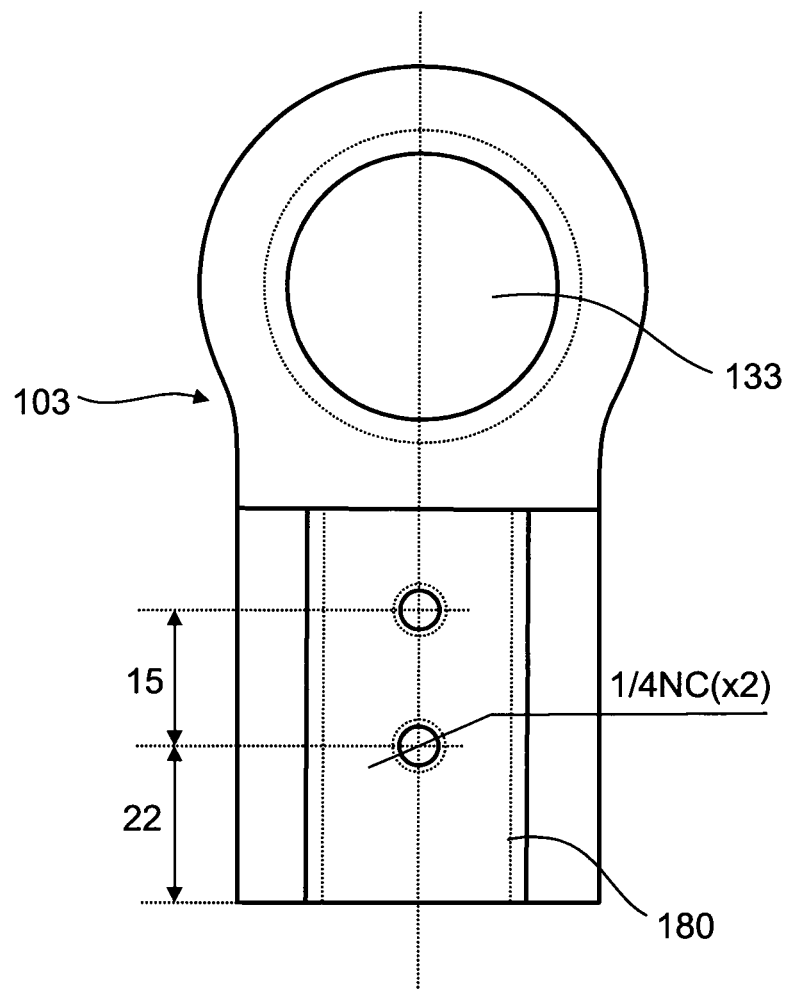
FIG. 5 is a schematic showing of a coupler for attaching the elements of FIGS. 3-4 to a microscope, in accordance with an exemplary embodiment of the invention.

A brief overview of the figures; FIG. 1 shows the complete BMS in operation; FIGS. 2-3B show sub-assemblies; FIG. 4A is a cross-sectional view of the BMS; FIG. 4B is an isometric view; FIG. 5 shows an optional adapter component; and FIGS. 6A-6D show various configuration options.

A main BMS 174 scans the beam in a raster pattern in, for example, shape, dimensions, raster scan speed, raster density and/or position and/or orientation on the eye tissue, which can be selected and controlled by the user. The scanned beam is then focused with a focusing lens (101, FIG. 4A) onto the treated tissue.

In the depicted embodiments (e.g., the OT-134 beam manipulating system), the 4 following sub-systems are provided:

1. Scanner

A beam scan mechanism 102 is used to create the raster pattern at preset shape, size, and the scanning parameters of the laser beam on the tissue as determined by the user. The scanner is driven by the controller (not shown).

2. Beam Combiner and Micromanipulator

A beam combiner and micromanipulator (MMP) 109 connects the OT-134 system to the ophthalmic microscope (OM, 106), optionally using an adaptor (e.g., 103, below), allowing the physician to use the OT-134 while viewing through the microscope. MMP 109 also combines the raster beam with the line of sight of the microscope, for example, using a path folding mirror 104. The micromanipulator portion of MMP 109 may be used to adjust (e.g., using a control lever 105) the combining and position the raster pattern at a desired exact position on the tissue.

3. Focusing Assembly

A focusing assembly 176 is optionally used for aligning the focusing of the laser beam and for aiding in aiming the beam and/or ensuring the beam is at focus on a treatment plane.

4. Adaptor

An optional adaptor 103 serves to couple the BMS to an Ophthalmic Microscope. In operation the BMS is typically attached to the OM used in the Operation Room. The OT-134 BMS is attached at the objective side of Ophthalmic Microscope 106.

In an exemplary embodiment of the invention, sub-systems 1-3 are integrated into one unit 107 (FIG. 3B). Optionally, unit 107 is further assembled from two parts, a scanner assembly 108 and a beam combiner 109. In an exemplary embodiment of the invention, combiner 109 also has a micromanipulator functionality allowing for manual repositioning of the targeted ablation area without moving the microscope, patient or beam combiner.

The Scanner:

In an exemplary embodiment of the invention, scanner 102 uses two perpendicular mirrors in a beam reflecting region 110, each mounted on a DC galvanometer ("galvo") or other angular actuator. By using two perpendicular actuators, the laser beam can be scanned by the two perpendicular mirrors to create variety of shapes, depending, for example, on the design and setting of the electronics that drives the two mirrors. Many suitable electronics are known and the controller optionally provides the control and/or power to the galvos, for example, via a cable 153, optionally extending to a power input 113 in a scanner housing 111. Optionally, the two galvos and mirror are installed in the same housing 111. Optionally, the articulated arm from a $CO_2$ laser 100 is connected to scanner 102 at a laser entry port 112. Alternatively, other beam scanning mechanisms, such as known in the art, for example, are used.

Optionally, laser port 112 is also used for inputting a visible aiming beam. In other embodiments, a separate aiming beam is not provided at port 112, optionally as part of a focus control mechanism, described below. In an exemplary embodiment of the invention, the visible aiming beam is designed to be co-axial and/or overlap with the CO2 laser beam.

In an exemplary embodiment of the invention, the galvo mirrors and the CO2 lens (in other parts of the system) are dichroic elements for the visible (red, in the range of 625-650 nm) and the $CO_2$ IR wavelength at 10.6 micron.

The diameter of a $CO_2$ laser beam exiting the articulated arm of a $CO_2$ laser system is typically a few mm, for example, 6-8 mm. For the ablation process the beam is optionally focused to a small spot, for example, less than 100, 200, 300, 400, 500, 600, 700, 900, 3000, microns in diameter. Optionally, using a small spot allows to better control and define the ablation area and/or to change the laser tissue interaction type and/or to increase the power density and allowing a faster raster rate for the same energy density required to achieve an ablation threshold. In an exemplary embodiment of the invention, a small spot is used to reduce the residual thermal damage created by the CO2 laser, for example, as described below. In an exemplary embodiment of the invention, focusing lens 101 is used for creating the small spot. Either a single lens or a set of lenses, or other suitable optical element, such as a diffractive element, or reflective optics may be used. Typically a spot size of 100 to 500 micron can be used. In the depicted embodiment a single lens with 200 mm focal length is used to provide a spot of 300-450 micron in diameter, which may depend, for example on the source laser parameters, such as beam uniformity, variability and initial diameter. Other optics may be used to modify the beam size. It is noted that in some embodiments of the invention the full sized beam is scanned, rather than a focused beam. Also, for other laser types different spot sizes may be desirable.

CO2 Laser Aiming Beam:

In an exemplary embodiment of the invention, a visible aiming beam is overlaid on the CO2 beam (or used when the CO2 beam is off) and is scanned with it. This beam can be used to visualize the spatial extent of area to be treated and/or scan path being followed. Optionally, this beam projects a pattern which indicates the boundaries of the tissue to be ablated when the ablation laser is next used. An optional focusing aiming beam is described below. It should be noted that, in some embodiments, the scanner has a relatively wide angular range and the aiming beam is generally shown only while in motion, even though it can be shown in stationary state. Alternatively, the aiming beam is powered even when the ablation beam is not emitted, for example, as soon is the system and/or ablation laser is turned on.

The aiming beam used for laterally positioning and monitoring the borders of the scan pattern is the aiming beam coming from a CO2 laser system, such as a Lumenis (Yokne'am, Israel) laser system 40C. It is collinear by design with the CO2 laser beam. Typically a HeNe or a diode laser are used. In the depicted system the aiming beam comes from a HeNe laser. Optionally, a green wavelength or other visible wavelength is used for the aiming beam.

Focusing Lens and Thermal Damage:

One reason for using focusing lens 101 is to reduce the residual thermal damage created by the CO2 laser. Thermal damage is caused to tissues where the temperature was high enough to cause biological damage such as coagulation, but not sufficiently high to cause ablation. The tissue is raised to this intermediate temperature when the energy absorbed by the tissue is not high enough to create ablation. Even if the power reaching the tissue is high, there is a possibility that the tissue will reach such "intermediate temperate". For example, this may happen (1) at the tail of the absorption depth of the laser radiation, (2) if there is a leakage of the thermal energy from the elevated temperature tissue to adjacent tissues. Whereas (1) is inherent to the absorption coefficient of the specific laser wavelength in the tissue, (2) is directly related to the time available for such "heat leakage" to take place. The longer the time—the more energy will leak (e.g., through conductance and/or fluid flow). The typical time for thermal energy to leak to the surrounding tissues is known as "the Thermal Relaxation Time" (TRT). Typical value of TRT may be on the order of 0.5-1.0 msec.

In order to minimize the thermal leakage to other (e.g., adjacent) tissues and cause thermal damage, it is desirable in accordance with some embodiments of the invention that the process of reaching the ablation temperature in the tissues to be removed occurs in a time duration shorter than the TRT. It is noted, however that if the energy delivered to the tissues to be removed by ablation is not high enough, that tissue will be heated but its temperature will not be raised enough to reach ablation temperature, and ablation will not take place. In an exemplary embodiment of the invention, this is met by a tradeoff of laser ablation parameters which allow to deliver enough energy to cause ablation, within a time scale that is less than the TRT, or another time constant and/or function thereof.

The use of the lens for focusing the CO2 laser beam on the treated tissue creates high power density (power per unit area) on the ablated tissue. This means that a high amount of energy may be delivered to the tissue in short time, in contrast to a situation of low power density where only a small amount of energy will be delivered to the tissue at the same time, and which may not be sufficient for ablation. Alternatively, to deliver enough energy to create ablation, a long exposure time of the tissue to the laser beam will be required to deliver the necessary energy to the tissue, which time may be longer than the TRT, and which in turn creates thermal energy leakage and thermal damage, as explained. In an exemplary embodiment of the invention, high power density and short exposure time to the laser beam is a preferred mode in creating ablation. In an exemplary embodiment of the invention, this combination is achieved in the LACS by using a focusing lens to create the necessary high power at the focus spot, and the scanner which rapidly moves the focused laser beam faster than the TRT.

In an exemplary embodiment of the invention, a long focal length lens is used to allow more working space under the objective for the operator who operates using the OM. The focal length of the focusing lens in the depicted system is 200 mm, equal to the typical focal length of the objective of typical OM's.

If the system does not operate at the correct focusing distance, the spot size of the focused beam becomes larger, power density is reduced and the risk of causing thermal damage (with or without ablation) may be increased. In addition, control of the scan dimensions may become less precise.

The Focusing System:

In an exemplary embodiment of the invention, longitudinal aiming for positioning the CO2 laser focus onto the plane of the tissue being treated is performed using a twin diode laser aiming technique. The beams from two visible diode lasers 130, (e.g. a wavelength of approximately 650 nm) are directed to converge to a single spot at the focal plane of CO2 laser focusing lens 101. Optionally, the output power of each of these diode lasers is in the range of 25 $\mu$W to 200 $\mu$W. Preferably the range is between 40 to 100 microwatt. In the depicted system the power of each laser diode is 50 microwatt. Optionally, the laser power is selected to avoid retinal or other ocular damage thereby.

In an exemplary embodiment of the invention, the lasers are focused, for example, each provided with a lens of focal length of 200 mm. Optionally, this causes defocusing at the retina, thereby reducing potential damage. Optionally or alternatively, this focusing increases their accuracy of use.

Optionally, the two separate aiming beams are never simultaneously directed at the same tissue point (e.g., a separation is optionally defined for when they are at a correct focal distance), but even if such a situation would occur the maximum total power would be less than 0.55 mW, still within the limit of Class II system. Alternatively, when the beams overlap, that is the correct focus. Optionally, the system is configured so that up to about 0.5 mm separation of the aiming laser light points, the focus is substantially acceptable.

In an exemplary embodiment of the invention, tiny alignment screws (e.g., 2 for each diode laser) allow the precise alignment of the lasers such that the two diode lasers overlap at 200 mm.

A potential advantage of such a aiming method over systems where the aiming beam is directed through the cornea such as photo-coagulators or Selective Laser Terbaculoplasty (SLT) systems, is that unlike the latter systems, in the twin beam aiming method the aiming beams can be directed towards the sclera and not through the cornea or onto the retina so excessive retinal exposure can not occur. Optionally or alternatively, the focusing is shown at the location of the desired focus, the upper surface of the sclera. While, optionally the focus aiming beams do not move, optionally they may be scanned with the scanner.

A potential advantage of such an aiming system lies in a way in which surgeons often use an OM in the OR (operating room). The surgeons often change the focusing setting and the zoom stetting during operation. It is very common that a surgeon will use different focusing distances as he maneuvers with the focus and zoom options of the OM. This is may be, at least in part because the eye optical alignment is not fully repeatable, even in normal eyes. Such deviation from time to time will cause the BMS to move out of its focus, even after it has been aligned once. It is therefore a potential advantage to have a simple method to monitor the focusing. Below is described a mechanism for correcting the focal length. An additional potential advantage is that a focusing element can be replaced to an element with a different focus and also a different matched set of focus aimer. Optionally, such a combination of lens and focusing beams is provided as a single unit.

In an exemplary embodiment of the invention, the BMS is mounted on apportion of the microscope which does not move with focus, zoom and/or lens changes of the OM and additional focal adjustment of the laser beam may be avoided after an initial focusing (e.g., absent patient motion).

In an exemplary embodiment of the invention, any necessary correction is applied by moving the scanner and its optics (which consists of the focusing lens of the CO2 laser and the two focusing diode lasers) relative to the MMP using a linear displacer, for example, a screw mechanism.

In the depicted system the screw mechanism is realized using a micrometer 115.

Optionally, the two optical systems, that of the OM and that of the BMS, should have overlapping focuses within the "depth of field" (DOF) of the BMS optics. DOF is defined as the axial distance along the optical axis of an optical system in which the focal spot size has not changed appreciably.

Typically, the DOF is related to the wavelength of the beam, the focal length of the condensing optics, and the diameter of the beam. The DOF may also relate to how tight the design is, in terms of tolerating certain changes in the spot size at the focal plane and still not jeopardize the essential performance characteristics of the optical system.

According to these guidelines, the DOF in the depicted system is in the range of +/−4 mm.

Taking into account the distance between the focusing diode lasers in the depicted system (39 mm) which are at the two sides of the ablation laser focusing lens, the focal length of the focusing lens which is 200 mm, and the depth of field which is +/−4 mm, the distance between the diode lasers focused spots of the Focusing System at the treatment area can be 780 micron apart (pre convergence or post convergence) at the treated tissue and still be within the DOF of the BMS.

In most ophthalmic microscopes (OM) the objective has a focal length of 200 mm. Optionally, the two optical systems, the one of the OM and the one of the depicted system, have the same focal lengths. If the operator observes that the spots of the two diodes coming from the focusing assembly do not overlap and are separated by more than the allowed distance as defined by the DOF, the operator can finely adjust the position of the $CO_2$ laser focusing lens using micrometer 115. This adjustment mechanism may also be used if the focal distances of the two optical systems (OM and BMS) are not the same.

A cross-sectional view of the ablation system is shown in FIG. 4A. An isometric view of BMS 174 is shown in FIG. 4B.

The Path Folding Mirror of the Beam Combiner:

The beam exiting the scanner and the focusing lens can be oriented to the desired direction using a path folding mirror 104 which is part of the MMP. The folding mirror is optionally connected to levers (e.g., 105) which can adjust the position and/or orientation of mirror 104, and thereby the exact position of the scan pattern on the treated tissue. In some embodiments the exact positioning of the scan pattern is crucial to the procedure, as ablation must take place in the desired location. Optionally, the manipulation is manual. Alternatively, one or more micromotors are provided and manipulation is remote, manually or automatically, for example using a computer. Optionally or alternatively, a remote and/or automatic manipulation system is provided for screw 115.

The Micromanipulator:

In an exemplary embodiment of the invention, the MMP has five screws for attachment onto the adaptor, in particular to a flange of a ring of the adaptor (542, FIG. 4B). Optionally, ring 542 is not a complete ring and/or does not overlap axially with the path folding mirror. In one embodiment, the ring is complete and does not reach down to the axial position of the mirror. Optionally, two sets of screws are provided, for attachment of the MMP in one position or in a flipped position.

This configuration allows safe attachment onto the adaptor and/or safe (e.g., without danger of disconnection) rotation of the BMS around the axis of the OM objective. As an example of such configuration, two screws 120 are fixed (e.g., glued). One screw 121 is used to complete the attachment of the BMS onto the adaptor, for example, by defining a triangle of points which define a diameter that is smaller than an outer diameter of the flange, for example, fitting in a groove or depression(s) thereof. Screw 121 is partially locked to the extent that it does not allow the BMS to be removed intentionally or un-intentionally (e.g. dropped by mistake). In this position, when screws 4 and 5 (122) are open, the user can rotate the BMS and bring it to the desired rotational position without risk of dropping; and when the BMS is at its desired rotational position screw 4 and/or 5 (122) are locked preventing incidental movement or rotation. Optionally, one or more screws is loosened a bit (and retightened) at a later time, to allow rotation of the BMS around the axis of the OM. In an alternative embodiment, two screws are maintained in a tight configuration and only one screw is loosened to allow rotation.

In an exemplary embodiment of the invention, the MMP has an opening 123 which is large enough so that when the BMS is attached to the adaptor and OM the operator can view freely through opening 123, except, possibly, for partial blockage at the beam combining mirror.

Optionally, opening 123 has a diameter typical to the diameter of the OM objective. In the depicted system the opening diameter is 45-50 mm in diameter. As shown, path folding mirror 104 is optionally mounted at the edge of opening 123.

In an exemplary embodiment of the invention, folding mirror 104 is wide enough (e.g., twice or more the width of the scanned laser beam, to reflect both the CO2 laser beam coming out of CO2 laser beam focusing lens 101 and the two laser diode 130 beams used for the focusing system. The width of the active area of the folding mirror may depend on where the mirror is positioned along the optical axis of the system. In an exemplary embodiment of the invention, the active area has a width between 20 and 70 mm. Optionally, the active area width in the range of 30 to 60 mm. Possibly the width is between 35 and 50 mm. In the depicted system the width of the path folding mirror is 39 mm.

In an exemplary embodiment of the invention, the folding mirror is coated with dichroic coating having high reflection in its active area both in the infrared (or other) range for the CO2 (or other) laser beam and the red range (~625-650 nm) for the aiming beams (or other wavelength, according to the color of the aiming beam). In an exemplary embodiment of the invention, the folding mirror can be coated in both sides. For example, this allows higher flexibility in configuring the BMS in all OR's: in right and left configurations, and back and front configurations.

In the depicted system described the folding mirror is mounted at the side of the beam entrance to opening 123. A potential advantage of this design is that the operator gains extra free working distance which is in the order of the MMP opening, as compared to a design where the mirror and its manipulators are distanced from the scanner and focusing optics. This extra working space may be needed for the operator to more easily operate and to reduce the risk of incidental touching unsterilized parts of the BMS.

Adaptor:

Adaptor 103 is a mechanical part used to attach BMS 174 onto the ophthalmic microscope (OM). In an exemplary embodiment of the invention, adaptor 103 is connected to the OM using a standard means, such as with screws and an interference fit of a tongue 180 in a matching groove in the OM, to the bottom of the OM near its the objective. Typically, threaded holes in the OM are factory prepared by the manufacturer of the OM specifically for attaching accessories to the bottom of the OM. Since different OM have different holes and threads for connecting the adaptors, different adaptors are optionally provided for different OM's. After the adaptor is attached to the OM, the micromanipulator is hooked onto the adaptor, for example, as described above. Optionally, adaptor 103 too has a round aperture 133 to allow the operator to freely look through and use the OM.

Scanner Control Unit

In an exemplary embodiment of the invention, the galvanometers are driven by electronic signals which create the desired patterns. The user can select the scan pattern (e.g. square, rectangular, arc) the exact dimensions of the pattern (e.g., with resolution of 0.2 mm), and the scan parameters (e.g. scan speed and raster line overlap). This is done by the controller (not shown). It should be noted that for some patterns, all of the scanning and ablation is on one side of the cornea. In others, such as a arc of greater than 180 degrees, the BMS may be rotated to allow ablations of the different parts or a scanning is performed in a pattern which avoids the cornea and/or the laser is turned off or blocked while the scanning overlies the cornea.

The OT-134 in the Operation Room:

In an exemplary embodiment of the invention, the LACS is attached to the OM in the OR using adaptor 103. It is also connected to the CO2 laser system through CO2 input port 112.

In some ORs the setting of the OR will prevent the positioning of the Laser system at the desired location for conveniently attaching the BMS to the CO2 laser system. In an exemplary embodiment of the invention, for example to increase the flexibility of configuring the BMS in the OR the, the BMS can be assembled in variety of configurations. In an exemplary embodiment of the invention, the BMS can be used with the CO2 laser system at its right, or left positions, at the front or at the back side of the operator.

FIGS. 6A-6D show various arrangements of controls on BMS 174. In an exemplary embodiment of the invention, manipulation lever 105, for example, can be connected to either a port 182 or a port 184. Similarly, micrometer 115 is optionally disconnected and reconnected at a desired side. Alternatively, scanner 102 with micrometer 115 is detached from adapter 103 and/or MMP (e.g., by opening screws 135) and then flipped and reconnected. Optionally or alternatively, MMP can be flipped and attached in mirror manners to an adaptor. This may require different placement of the screws in the MMP and/or a longer flange on the adaptor.

It should be noted that FIGS. 6B and 6D show adapter 103 not coupled to BMS 174.

A LACS can be designed with other modular components that can be attached to each other in various configurations according to geometrical needs. Optionally or alternatively, such modular components can be replaced according to need, for example, an adapter changed to match an OM objective design or a focusing assembly replaced to match a desired focal length, a scanner replaced to match a desired range of movements or a MMP (or only a mirror portion thereof) replaced to match a microscope field of view size and/or wavelength of various aiming beams that are used of aiming. In an exemplary embodiment of the invention, the parts that are modular are designed to be disconnected and reconnected with a minimum of work and without substantially affecting alignment, for example, only requiring opening and closing of fewer than 5 screws and/or having interlocking and/or matching surfaces which ensure a known alignment of optical elements. Optionally or alternatively, some simple calibration tools are provided, for example, the manual micromanipulation and focus control.

Figure 7A:
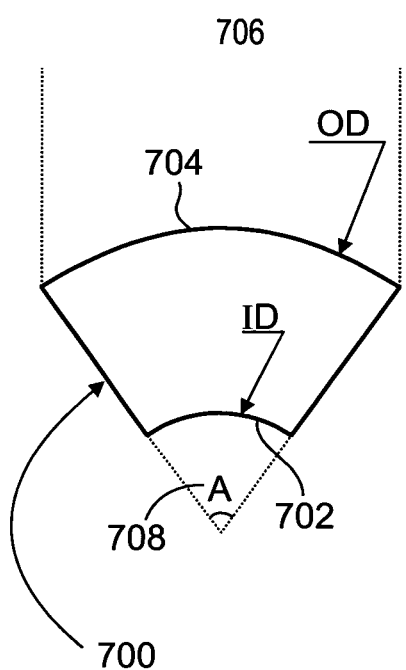
FIGS. 7A-7D illustrate optional scan paths that generally conform to the shape of a limbus, in accordance with an exemplary embodiment of the invention.

Scan Patterns:

The scanner can create various scan patterns. For example, such patterns can include:

Square, rectangular, Sectored disc (700, FIG. 7A) and concave shapes.

The sectored disc (SD) is a curved pattern, that follows the eye curvature of the cornea, iris or limbus, for example. The SD is defined by the two Diameters of the inner (ID, 702) and outer (OD, 704) circles of which the disk is a sector, and the width 706 of the sector, which may also be seen as an angle ! (708). The scan pattern border need not have exact arcs of a circle and may have other shapes, like an arc of an ellipse or a free-form curve.

Figure 7B:
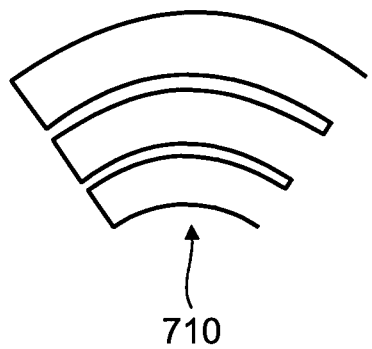
Figure 7C:
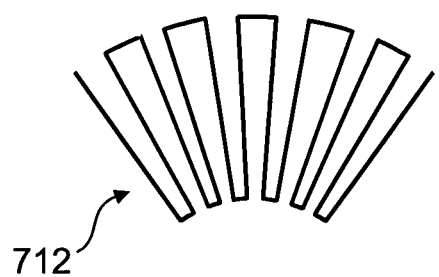
Figure 7D:
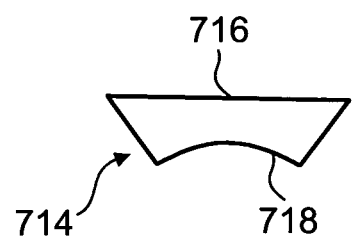

Various scan paths may be used within the pattern. One example is an x-y raster. FIG. 7B shows a scan path 710 where the scanning is in curved lines, optionally parallel to the curvatures of the scan shape. FIG. 7C shows a scan path 712 with the scanning direction perpendicular to the curves. Optionally, overlap between spots in uniform in scan path 710, and non-uniform in scan path 712.

FIG. 7C shows a scan shape 714 with a limbus conforming curved concave border 718 and a straight or otherwise non-parallel distal border 716.

In an exemplary embodiment of the invention, the SD can be programmed to create discs with ID and OD in the range: 4.0 mm (or 8 mm)<ID<15.0 mm, OD<17.0 mm (or 20 mm), which cover the range of typical human eyes. Other sizes, smaller or larger may be used as well. Width is, for example, between 1.0 and 7.0 mm, optionally between 1.0 and 5.0 mm. In the depicted system, width is between 1.0 and 4.0 mm.

In an exemplary embodiment of the invention, it is noted that when ablating large areas, a rectangle is a poor approximation of the scleral area above the Schlemm's canal and this may lead to greater danger of perforation. Optionally, a plurality (e.g., 2-5) of smaller (e.g., 0.7-2 mm in length) areas are individually ablated. Optionally or alternatively, a curved form is used to match the shape of the limbus/cornea.

Enforced Delay

In an exemplary embodiment of the invention, the computer control system does not act on an ablation command if a repeat delay time did not pass since the last ablation. Optionally, this delay is a parameter, for example, provided on a memory card. In an exemplary embodiment of the invention, the delay is selected so as to be long enough to allow clinically useful percolation to be identified in an ablation area. Optionally, the delay is not so long as to allow non-clinically useful percolation to be mistaken for clinically useful percolation. Optionally, the delay is between 1 and 15 seconds, for example between 1 and 3 seconds.

Exemplary Methodology of Identifying the SC Position:

The inventors have discovered that if the anterior perimeter line of the scan pattern is positioned over the limbus, after the flap was created, the SC (Schlemm canal) is repeatedly exposed if the width of the scan pattern is 1.4 mm, e.g., along the direction which extends away from the cornea and limbus. In an exemplary embodiment of the invention, this consideration is applied to any treatment of the Schlemm canal for any type of non-penetrating filtration surgery (e.g., other lasers, manual or automatic) are aimed for such a region. Optionally or alternatively, such surgery is carried out in two steps. A first step where the entire suspected area is ablated to a certain depth, for example, a fixed depth or until the Schlemm canal (SC) becomes visible, e.g., based on the beginning of percolation thereof (e.g., percolation that takes several seconds to cover the surface). Optionally, when the SC is exposed the width of the ablation area is reduced to, for example, between 0.8 and 1.2, for example, 1 mm overlying the SC. Optionally, the length (e.g., along the curvature of the limbus) is also reduced at this time, for example, to 1-2 mm.

Optionally or alternatively, the scanning is performed in small sub regions (e.g., 2, 3, 4 or more), for example, 1-2 mm in length (around the circumference of the eye). In each such region, the SC may be detected separately and/or ablation be carried out to different depths.

Although the typical width of SC is approximately 350 micron, it may be advantageous to create a narrower or wider percolation zone (e.g., 0.2, 0.3, 0.4, 0.5, 0.7, 1, 1.5, 2 mm, or intermediate or greater width) such that percolation can take place from the SC and its neighborhood zone. Optionally or alternatively, a separate reservoir is created, or the zone is made wide enough to reduce adhesions between the flap and the percolation zone.

Eye Protector:

In order to prevent incidental irradiation of the CO2 laser beam, the operator optionally uses an eye protector, which covers the cornea and is made of material that absorbs or reflects CO2 radiation, thereby substantially attenuating and/or completely blocking undesired radiation from reaching sensitive parts of the eye which are not supposed to be irradiated.

An example for such eye protector is a contact lens which may constitute water in a concentration of above 40% or above 50%. In an exemplary embodiment of the invention, the high concentration of water improves the blocking properties of the eye protector. Optionally, the protector is a section of a sphere or is a curved rectangular element, and is optionally sized to fit an adult eye. The protector is optionally held in place by a temporary adhesive. Optionally, the lens has a thickness of less than 3 mm, less than 2 mm or less than 1 mm. Optionally or alternatively, the lens is placed over the pulled back flap and optionally includes a depression therein to receive the flap.

Optionally, further blocking properties may be achieved if the eye protector has selective transmission properties, by which the aiming beams that emit at the red parts of the spectrum are blocked by the eye protector as well as the CO2 laser in the Infrared. Optionally, however the eye protector is transparent enough to allow the operator to view the inner part of the eye during operation. This transparency may assist in monitoring the status of the eye during operation.

Such selective transmission can be realized by doping the eye protector which is otherwise transparent to the visible light (such as contact lens) with a dye (blue, purple) that selectively absorbs the red aiming beams.

In an exemplary embodiment of the invention, the protector includes an aperture (e.g., on the order of the size of the ablated area, or twice the size in one or two dimensions, optionally, not over the cornea, optionally having a curved shape following the cornea) for the CO2 radiation to path through and/or includes a section with lower reflection or absorption, for example, having a reduced water content and/or thickness.

Exemplary Surgical Procedures

Figure 8:
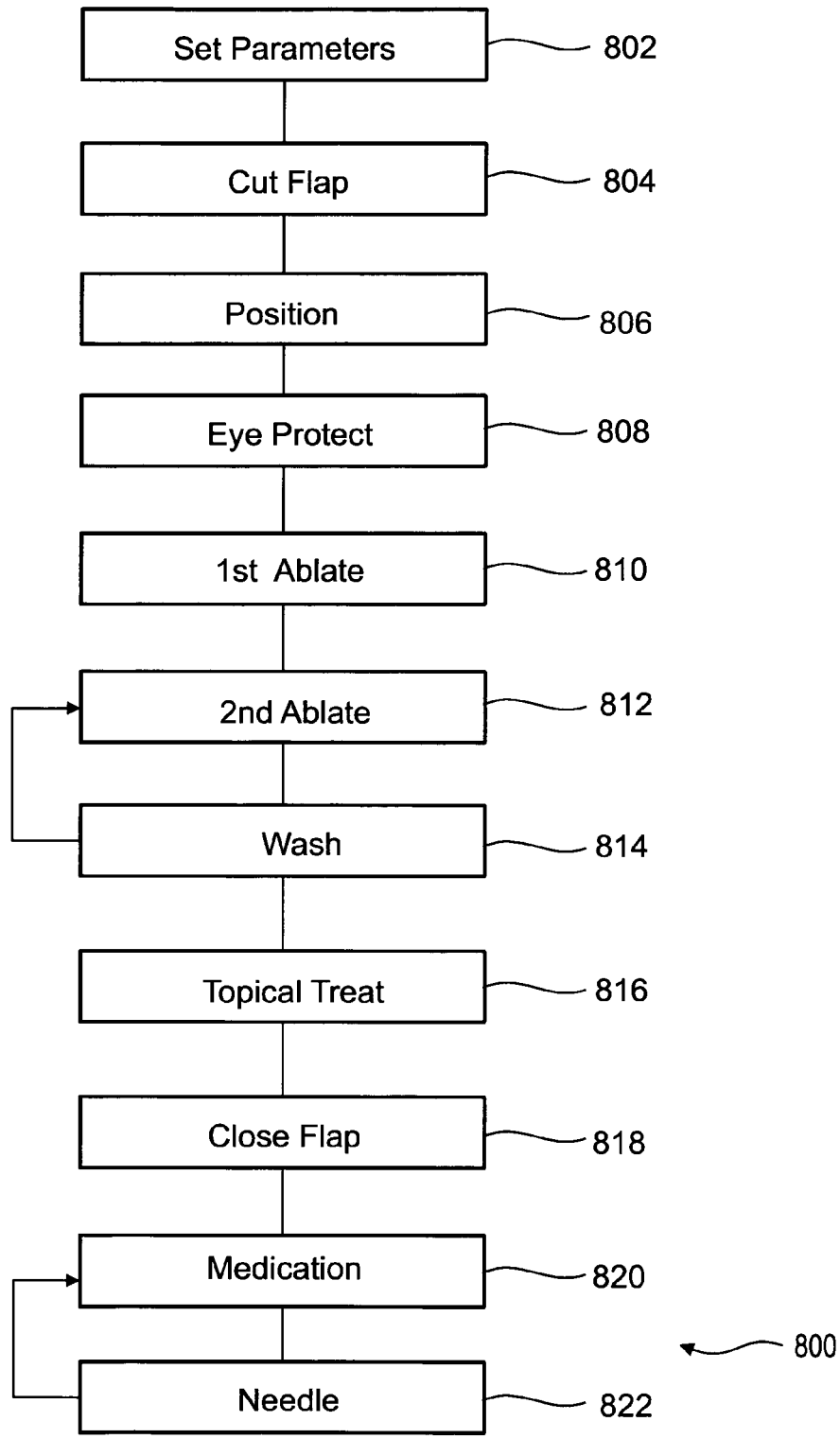
FIG. 8 is a flowchart of a method of treating an eye, in accordance with an exemplary embodiment of the invention.

FIG. 8 is a flowchart of a general procedure 800 for eye treatment, in accordance with an exemplary embodiment of the invention. After a brief description, a detailed description of exemplary procedures will be provided.

At 802, various laser and scan parameters are optionally set or selected. At 804, a flap is cut in the scleral tissue overlying the Schlemm canal. The order of the two acts may be changed, as can be the order of other of the acts decided below. At 806 the laser beam operational field is positioned at a correct location on the eye (e.g., 1.4 mm over the Schlemm canal). At 808, an eye protector is optionally provided on the eye, with a window exposing the treatment area. At 810 a first ablation is carried out until the Schlemm canal is nearly exposed and percolation starts. At 812, further ablation is more limited to areas above and adjacent the Schlemm canal. At 814, the ablation area may be washed between ablation acts. At 816, the ablation is completed and a topical treatment, such as anti-inflammatory or other bioactive material or a spacer may be provided at the ablation area. At 818, the flap is closed, optionally, with one or two sutures at either end of the exposed Schlemm canal. At 810, topical medication may be provided after the procedure, for example, for several days and weeks. Optionally or alternatively, systemic medication may be provided or IOP-reducing medication may be provided. At 822, a needling procedure, where a small object is placed in the ablated region and optionally moved around to separate and/or reduce adhesions between the flap and sclera, may be applied. Optionally or alternatively, the eye may be punctured to reduce pressure. It should be noted that such needling and/or puncturing are optionally applied after the procedure is completed and possible the tissue healed, for example, to combat adhesions and/or other causes of reduced percolations. Such times may be, for example, several weeks or months or years and are optionally performed in response to a measured increased IOP.

Exemplary Specific Procedure and Aftermath

Typically, surgeries are performed in the ophthalmic surgery room, under local anesthesia (e.g., retrobulbar, peribulbar, sub-tenon, or topical), unless there is an indication for general anesthesia.

1. Following routine preparation of the eye for sterile surgical conditions a speculum is placed.

2. A fornix-based peritomy is performed at the superior limbus, and the Tenon's capsule is also dissected, to expose the sclera. The location of the flap is optionally under the upper eyelid.

3. Optionally, careful hemostasis is performed using cautery.

4. A partial thickness (e.g., approximately one half) limbal-based scleral flap is dissected at the limbus into clear cornea. The length of the flap is, for example, between 2 and 6 mm. Optionally, the length of the flap is between 4 and 6 mm. The length of the flap is, for example, between 2 to 6 mm. Optionally, the length of the flap is between 3 and 5 mm. Optionally, the length of the flap is approximately 4 mm.

5. The desired shape for the scanning area is set. Optionally, the shape of the scan pattern is rectangular or square or that of a sectored disc or arc.

6. The appropriate scan area size is set.

7. Laser beam focusing is carried out.

8. The treated area on the patient is defined.

9. The laser power is optionally verified. In an exemplary embodiment of the invention, the laser power at the laser entrance port of the Beam Manipulating System is between 18 to 30 watts. Optionally, this power is between 20 and 26 watts. Optionally, the power is between 22 to 24 watts.

10. Laser mode is verified. Optionally, the laser mode will be Continuous.

11. Optionally, The focus of the laser beam on the targeted area is verified using the BMS focusing assembly.

12. The cornea is protected against an incidental irradiation by the CO2 laser. Such protection can be made by way of example using soft contact lens which absorbs the CO2 radiation. Optionally, this contact lens contains more than 50% water. Optionally or alternatively, the Cornea is protected against incidental radiation of the visible aiming beam(s). By way of example, same eye protector can protect against visible light and against infrared radiation. Optionally, the eye protector is made of contact lens material and is tinted with color to substantially attenuate the visible radiation.

13. The treated area is verified by observing the pattern of the red HeNe laser aiming beam of the $CO_2$ system.

14. The laser is switched to READY. The surgeon verifies that the laser READY light indication illuminates.

15. A footswitch may be pressed to activate the ablation. Optionally, the scanning is continuous and optionally synchronized with the laser (optionally by synchronization with the laser shutter) so that whenever the laser is turned on, it is scanned according to the pattern without need for communication between the controller and the laser source. Optionally, such communication is used. The first ablation scanning (step) is verified to be done properly.

16. The HeNe aiming beam indicates the ablation area. The dimensions of the indicated ablation area should include the Schlemm's canal area. If rectangular or square or arc patterns are used, the 2 anterior red dots of the aiming beam or the anterior line (e.g., dots added at the anterior two corners of the ablation region, which assist in alignment thereof with the limbus) are optionally placed on the limbus line prior to first ablation. Optionally, the ablation pattern length is between 1 and 5 mm. Optionally, the length of the scan dimension is between 2 and 4 mm. Optionally, the length of the scan dimension is between 2.5 and 3.5 mm. The width is, optionally, 1 to 3 mm long. Optionally, 1 to 2 mm. Further optionally, 1.2 to 1.8 mm. If a sectored disc is used the concave edge of the pattern is overlaid on the limbus.

17. Wait at least 1-2 seconds between consecutive ablations. Optionally, the ablation is also used to seal any blood vessels that leak, for example, as an automatic consequence of the scanning. Alternatively, the laser is separately used for such sealing. Optionally the system is designed (e.g., as described above) to electronically prevent the repeated ablation within a time period of, for example, less than 1-2 seconds (repeat delay), thereby ensuring that the percolation can take place and the physician and/or a computerized imaging system had time to detect percolation, if any. In many cases, it appears that if significant percolation does not appear within 2 seconds, such percolation does not appear.

18. Performing repeated ablations until the outer wall of the Schlemm's Canal is ablated. In an exemplary embodiment of the invention, the laser parameters are selected to minimize thermal damage to the bottom of the ablated area, through which percolation is expected.

19. The surgeon may work separately on the scleral bed formation with the laser and on the percolation zone above the Schlemm's canal area. The scleral bed size is optionally about 4×3 mm$^2$.

20. The charred tissue is optionally wiped with a wet sponge every 1-3 laser scans. Alternatively, a spray may be used 21. Optionally, the laser parameters are modified as required within the recommended working parameters detailed in the above, for example, responsive to rate of ablation or amount of fluid or thermal damage observed.

Operating the OT-134 system is optionally continued until sufficient percolation is achieved. While the laser procedure is stopped when the surgeon decides that sufficient percolation is achieved, it is recommended in some cases that the total length of the percolation zone is at least 3 mm long and at least 0.5-1 mm wide.

22. The scleral flap is optionally repositioned and secured in place using 2 interrupted 10-0 nylon sutures.

23. Healon 5 high molecular weight Ophthalmic Viscosurgical device (viscoelastic substance) is optionally applied beneath the repositioned flap. Other spacers and/or spacer materials may be used here.

24. The conjunctiva is optionally repositioned and secured in place using interrupted 10-0 nylon sutures.

25. Antibiotic and steroid ointment are applied and the eye is optionally closed with a patch and a shield. Optionally, the use of anti-metabolite drugs (such as Mitomycin C and 5-FU), and/or spacers (such as the STARR Collagen drainage device, e.g., degradable or permanent) is optional, e.g., per physician discretion. The use of paracentesis and/or an anterior chamber maintainer is optionally left to the physician's discretion.

Exemplary Post Surgical Management

1. Post-operatively the patient is optionally treated with topical corticosteroids (e.g., Pred Forte drops) at least every 3 hours during waking hours for one week, and then every 6 hours during waking hours for additional 5 weeks. At the end of the steroid treatment, it is in the physician's discretion to stop or to taper off the steroid treatment.

2. Optionally, after 2-4 weeks of steroids, NSAIDS treatment is initiated; Optionally, Voltaren Ofta is administered.

3. One week or more postoperative, if the physician believes, at his/her discretion, that the post index IOP is too high for the patient, the steroid treatment is optionally stopped and NSAIDS treatment (e.g., Voltaren Ofta), is begun. If IOP is reduced to an acceptable level, the corticosteroids treatment is optionally resumed.

4. When NSAIDS treatment is initiated, this treatment is optionally administered for 8 weeks.

5. Post-operatively, topical antibiotic treatment such as 4th generation fluoroquinolone (e.g. Vigamox), is optionally administered, for example, 4 times daily, for 2 weeks.

In an exemplary embodiment of the invention, the usage of gonio-lens is avoided in the first 3 weeks post procedure unless IOP increases to values >18 mmHg. If performed, a 4 mirror gonio-lens is optionally used.

1. Goniopuncture is an optional measure to reduce the IOP. This measure is also optionally preserved for cases that failed to respond to the other measures described above. The decision to perform the procedure and its timing is by physician discretion and is typically several days, weeks or months after the laser ablation procedure.

2. Needling (separating the flap from underlying scleral tissue using a needle that is inserted between them and moved) is another optional measure to reduce the IOP and/or adhesions. The decision to perform the procedure and its timing is by physician's discretion and is typically after healing is complete or nearly complete, for example, to combat adhesions.

3. Anti-glaucoma medications may be used at a physician's discretion.

4. Using anti-metabolites during needling is at a physician's discretion.

Notes:

1. In an exemplary embodiment of the invention, the flap length is selected to be between 4 to 6 mm, as, with a broad flap one can create a broad percolation zone, which in turn may be more effective in relieving the intro-ocular pressure than a narrow flap. Optionally, the ablation area encircles at least 10, 20, 30, 60, 90, 180 or more or intermediate degrees of a circumference of the cornea.

2. Optionally, for example, because the sclera has inherent in-homogeneities, it may be useful to perform consecutive ablations of smaller areas than to perform a full length ablation throughout the flap length. Optionally, each such small area is 2 to 3 mm's long, within a flap length which is 5-6 mm long.

3. Optionally, the ablation is performed above (and optionally along) the Schlemm's Canal (SC), which is the region where percolation takes place in normal people.

Typically, the SC is covered by scleral tissue, and its position cannot be indentified precisely a-priori. Optionally, the following method is used to determine its location: The flap is raised, and the limbus is exposed after the formation of the flap. It may be useful to identify the limbus after flap formation because the position of the flap is often not the same along the thickness of the sclera.

Alternative System (OT-133)

Figure 9:
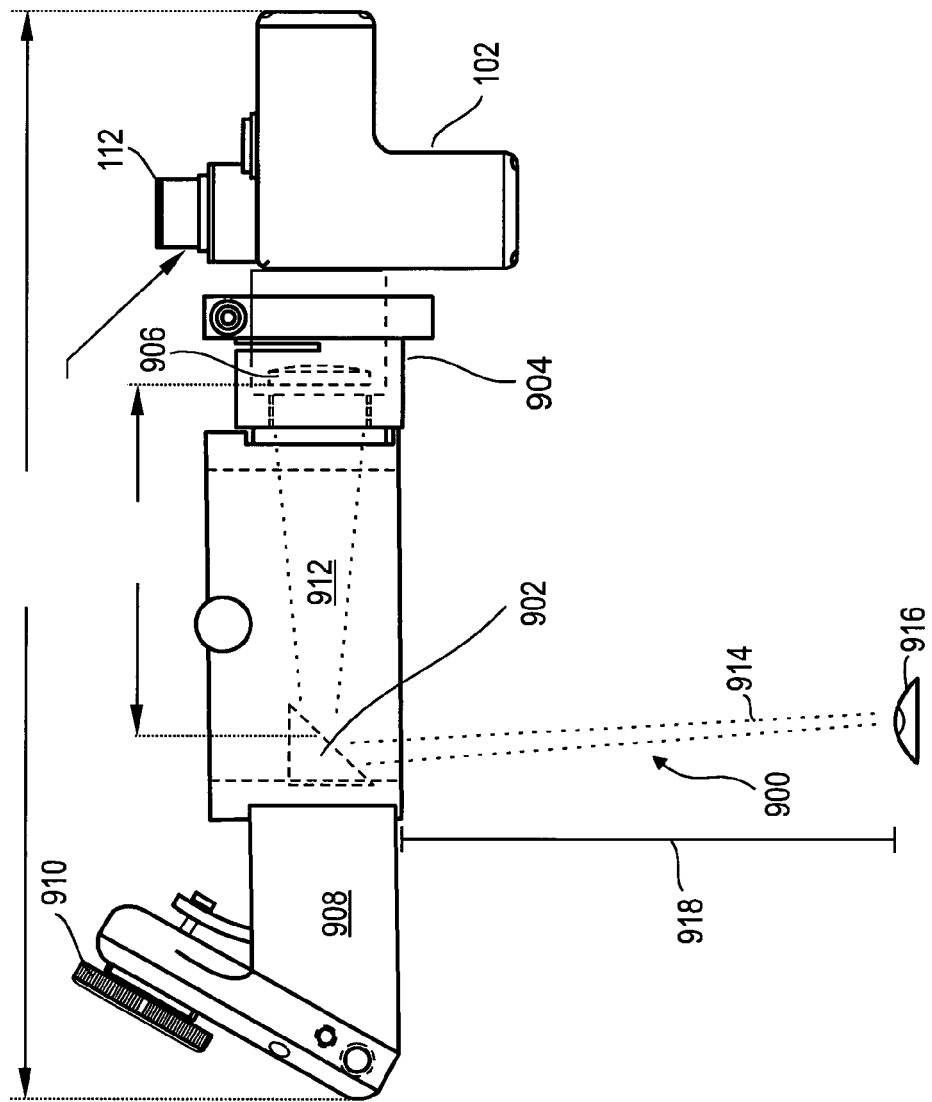
FIG. 9 is a schematic top view of a design of an alternative BMS, in accordance with an exemplary embodiment of the invention.

FIG. 9 shows an alternative system 900 for laser ablation control, which was evaluated in preclinical and in clinical trials.

In this system, a path folding beam combining mirror 902 is placed opposite of an output of a beam scanner 102. A focusing system 904 includes a lens 906, for example, as described above. Manipulation of mirror 902 is via a micromanipulator 908, for example using a knob 910, mounted on an opposite side of an aperture 912 from scanner 102. Aperture 912 is optionally aligned with a field of view of an OM (not shown). In an exemplary embodiment of the invention, the scanned beam 914 has a width of, for example, 0.3 mm when it impinges on an eye 916. Optionally, a distance 918 between system 900 and the eye is shorter (e.g., 100-120 mm), for a same lens 906, as compared to the OT-134, described above.

Evaluation, in a pre-clinical phase (Reference—Assia E I et al) included three experimental models: enucleated sheep and cow eyes (n=18) to determine optimal irradiation parameters, live rabbit eyes (n=20) to test feasibility and cadaver eyes (40 procedures in 20 eyes) to study effects in human eyes tissue. After a half-thickness scleral flap was created, deep sclerectomy was performed by CO2 laser applications on the scleral bed down to the trabeculo-Descemet's membrane.

Results: Fluid percolation was repeatedly achieved without penetration in sheep and cow eyes using scanned laser energy of 5-10 W at a pulse duration of 200 microsec and a working distance of 25 cm. In live rabbits, deep sclerectomy was achieved without perforation in 19/20 eyes. Intraocular pressure was significantly decreased on the first postoperative day (10.3+/−5.1 mmHg lower, on average, than in the non-operated fellow eye; P<0.001), and this persisted for 21 days. Operations on all cadaver eyes resulted in effective fluid percolation. Penetration of the scleral wall occurred in five cases only after repeated laser applications with high energy. Histologically, a thin sclerocorneal intact wall was demonstrated at the sclerectomy bed. Collateral tissue damage did not extend beyond 100 micron, and adjacent structures remained unharmed. This preclinical phase shows that CO2 laser-assisted deep sclerectomy is a feasible and apparently safe procedure.

The clinical phase included an evaluation of safety and short term performance on 23 glaucoma patients in multi national multi central trial. All patients had POAG or PEXFG.

The Results:

Fluid percolation was achieved in all cases

No significant complications related to the laser treatment were observed

The anterior chambers were deep and stable in all case, even when the IOP was low.

On day 1 all of the cases, except one with acute inflammatory reaction secondary to an intra-operative event, had IOP lower than 12. In 16 out of the 20 cases the IOP was 7 mmHg or lower.

The results indicated that achieving the surgical goal (fluid percolation) and short-term effect (low IOP after surgery) is feasible and practical using the OT-133 system.

The Success Rate of the 23 Patients:

The system demonstrated safety and short term efficacy.

5 patients dropped out due to mistakes in the procedure (e.g., and converted to trabeculectomy) and protocol deviations Success criteria defined as IOP under 22 mmHg.

Figure 10:
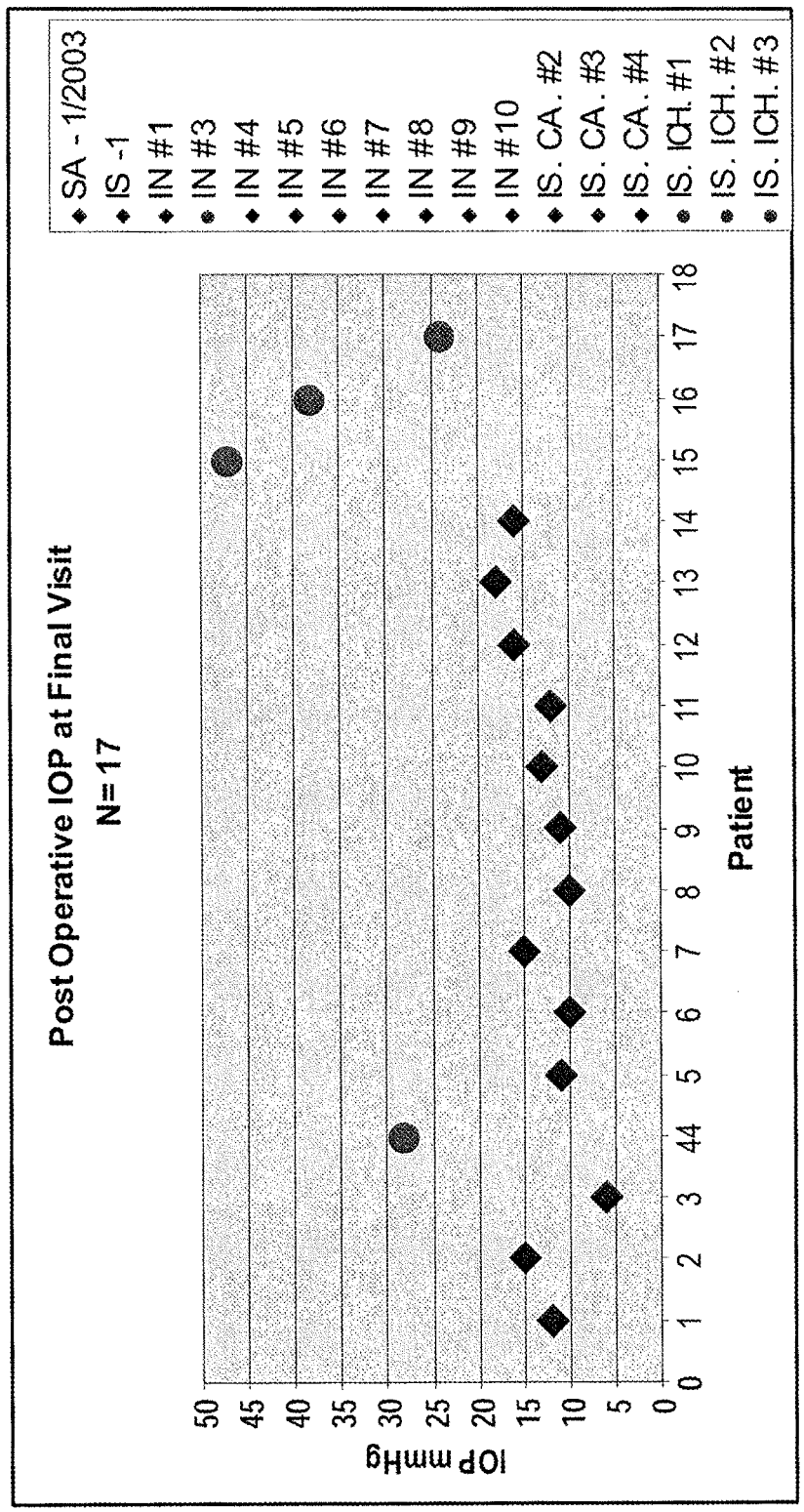
FIG. 10 is a chart showing experimental results for a device in accordance with the alternative design of FIG. 9.

The success rate at 6 months was 76.4% (see also FIG. 10).

OT-134 Testing

The OT-134 was tested in a similar dual phase way: Pre-clinical and clinical studies.

The objective of pre-clinical study was to verify the safety of the improved device (OT-134) when used for scleral tissue ablation with possibly more optimal combinations of laser power level, scanner dwell time and overlap values within a specified range of parameters.

The pre-clinical phase included three experimental models: enucleated pig eyes (n=60), live rabbit eyes (n=24) and human cadaver eyes (40 procedures in 20 eyes) to study effects in human eyes tissue.

The enucleated pigs' eyes were used to determine possible scleral flap and scanning area dimensions. The objective was to determine the scanning area dimensions that will reveal the Schlemm's canal while avoiding ciliary body damage. Four flap widths were examined: 3, 4, 5, and 6 mm.

The trial on human cadaver eyes also used to determine the dimension of the flap size (3, 4, 5, and 6 mm width) and the scanning area width of each laser application was up to 90% of the flaps' width (optionally between 40% to 60% of the width) and the scanning (anterior-posterior) area of each laser application was 5 sqr mm to 20 sqr mm possibly up to 1.4 mm from the posterior limbus line. In some embodiments of the invention, the scanned area is between 2 and 20 sqr mm, for example, between 2 and 10 sqr mm. The anterior two aiming beam are laid on the posterior margin of the limbus, and a length of 1.4 mm of the scanning area—revealed as containing the Schlemm canal were ablated, possibly enabling the physician to expose the canal in a simple, safe and easy manner. Laser treatment in that area gradually ablated the superficial scleral layers one by one revealing the Schlemm's canal. Once Schlemm's canal was recognized, the scanned area dimensions were gradually reduced. This shows that two stage ablation, with different ablation areas, can be used.

In the next stage the system was tested (for safety) on a group of 12 rabbits (24 eyes) divided into 4 subgroups, according to follow-up duration until sacrifice (4 rabbits were sacrificed immediately following procedure (upon recovery), 3 were sacrificed 10 and 15 days after procedure, respectively and 2 were sacrificed 21 days post procedure). Both eyes were operated on in each rabbit. Recommended range of laser and scanner parameters were used in all procedures (Laser power range of 20 W to 26 W was used; Scanner dwell time was set to 100 to 400 μsec, and 10% to 40% beam overlap of diameter in all cases). Various shapes and dimensions of scleral ablation area were examined (e.g., rectangle, slotted disc).

Results: Twenty-four eyes of 12 New Zealand White rabbits were operated on. Laser power was 24 W in 20 procedures, 22 W in 2 procedures, 20 W in 1 eye and 26 W in 1 eye. Percolation was repeatedly achieved, except for one eye, in which laser application was too posterior from the limbus. In 1 eye (#2699 left eye, group 1.1) an inadvertent ocular penetration was done with the crescent knife during flap creation, and therefore not treated with laser. Micro-penetration of the scleral wall occurred in 4 (17.4%) eyes.

These experiments showed that the learning curve is short and the procedure can be generally safe and simple. Optionally, there are no special requirements for the OR (e.g., the same needs as for cataract and/or trabeculectomy).

The procedure is safe and simple.

During the post operation recovery period, the interface between the ablated sclera and the flap was filled with blood and plasma. In eyes examined immediately post-operation, inflammatory cells were observed. Ten days post operatively, the crater was filled with connective tissue. Thermally damaged tissue shrunk in size. Thermally damaged tissue almost disappeared. Twenty days after the procedure, trabecular meshwork (encircled) underneath the scar did not show any signs of thermal damage.

Thermal Damage

In some experiments with the OT-133 failure was associated with PAS formation. PAS formation can possibly be attributed to thermal damage. Heat generated during the tissue ablation possibly causes local inflammatory reaction leading to tissue adhesions and scarring. In an exemplary embodiment of the invention, decreasing and controlling local tissue inflammation improves the long-term results of the $CO_2$ laser filtration procedure.

In all examined eyes, certain thermal damage was seen on lateral wall of ablation crater following the procedure. However, it was found that for some operating parameters, substantially no thermal damage was present in the floor of the crater, made up of loose trabecular meshwork, where percolation takes place.

Histological studies demonstrated a deep crater in the scleral wall down to the trabeculo-Descemet membrane, with no perforation. Neighboring structures, including the iris root, ciliary body, adjacent sclera and cornea, were not affected and remained undamaged. No inflammatory cells were present 10, 15 and 20 days following the procedure and no significant differences were noted in tissue response 10, 15 or 20 days after the procedure. Thermal tissue damage up to 200µ could be detected merely at the lateral walls of the ablated sclera. The trabeculo-descemet membrane was free of thermal damage.

Figure 11A:
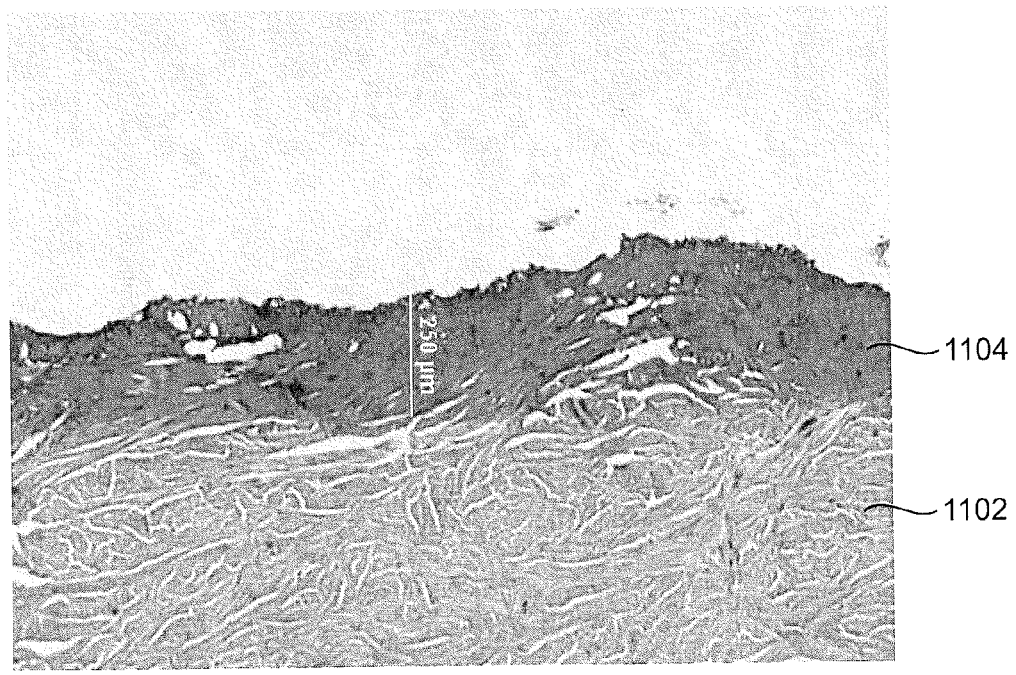
FIG. 11A and FIG. 11B are images of cross-sectional views in eyes, showing different amount of thermal damage for different laser settings, in accordance with an exemplary embodiment of the invention.
Figure 11B:
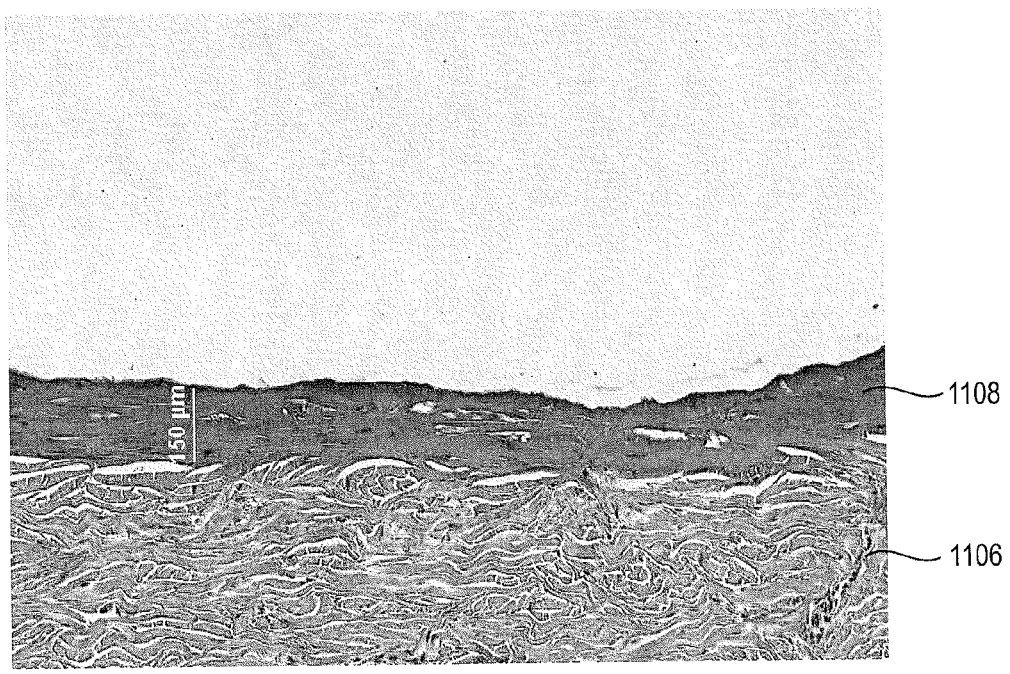
Figure 11C:
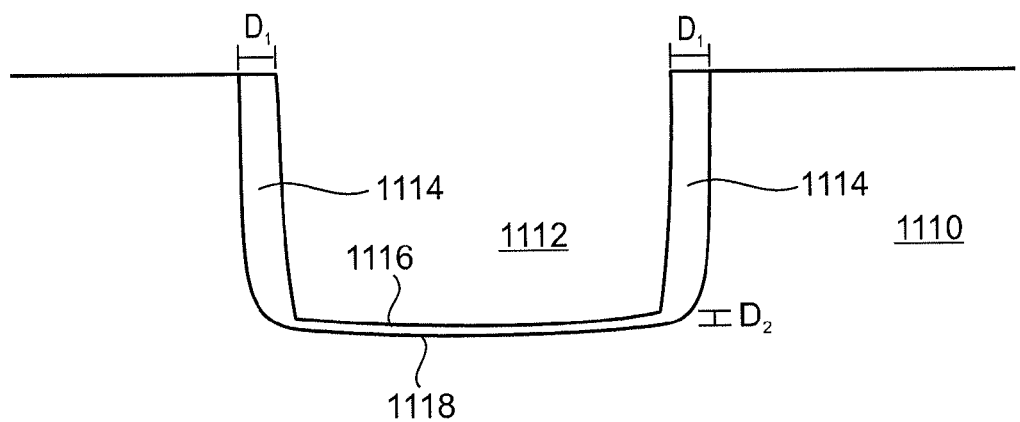
FIG. 11C schematically illustrates different amounts of thermal damage in different parts of an ablation crater in accordance with an exemplary embodiment of the invention.

This is illustrated in FIG. 11C, where a thickness of thermally damaged tissue 1114 at the sides of a carter 1112 in scleral tissue 1110 is greater than damaged tissue 1116 at a bottom 1118 of the crater. The crater is the vacant space in the sclera above the Schlemm's Canal (SC) created by the removal of the sclera by ablation, the bottom being the intact thin layer above the SC.

FIGS. 11A and 11B illustrate reduced thermal damage for some parameters over others for non-percolating tissue. FIG. 11A shows a histology of tissue ablated using 18 watt, dwell time 500 microseconds and overlap of 20% (using OT-133). The thickness of thermally damaged tissue is about 250 microns. FIG. 11B shows a histology of tissue ablated using 24 watt, dwell time 220 microseconds and overlap of 20% (using OT-134). The thickness of thermally damaged tissue is about 150 microns.

The parameters of the scanning were selected based on very extensive pre-clinical trials on pig eyes, alive rabbit eyes and cadaver human eyes. Generally, ideal parameters for the procedures with the OT-134 were found to be energy of 24 watt, dwell time of 200-300 µsec, (e.g., 300 microseconds) and overlap of 30%.

The experimentation also showed potential advantages of using the OT-134 with the determined and control focus, stability and correct parameters of working results in reducing thermal damage to the tissue as demonstrated by the Comparison of scleral thermal damage depth at different operating parameters (e.g., FIGS. 11A and 11B).

The clinical phase of the OT-134 device was preformed as a multi-centered, multi-national clinical trial, performed at 3 sites:

14 laser assisted non-penetrating deep sclerectomy procedures, preformed at the APEC hospital, Mexico-city, Mexico.

Thirteen subjects were treated at the Siloam Eye Hospital, Madanapalle, India.

Ten subjects were operated at the East-Sight Recover Center in Moscow, Russia.

Results are described below.

Overlap

Figure 12:
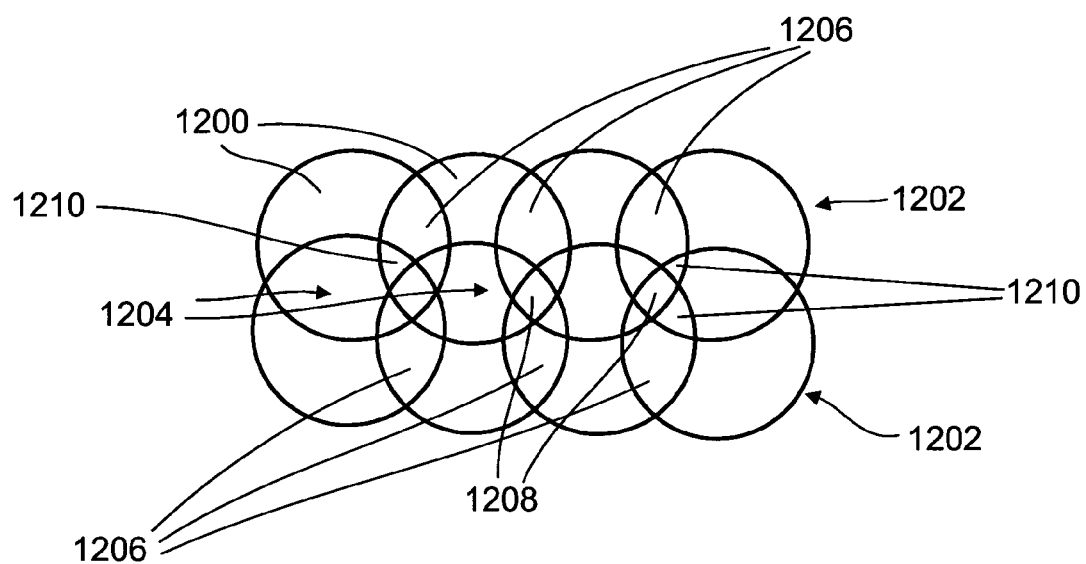
FIG. 12 shows an exemplary overlap in two dimensions between treatment spots, in accordance with an exemplary embodiment of the invention.

FIG. 12 illustrates overlap between spots, in accordance with exemplary embodiments of the invention. A plurality of laser spots 1200 overlap (e.g., as measured by distance between beam centers as compared to beam diameter), at overlaps 1206 between spots in a row 1202, overlap regions 1204 between rows 1202 and multiple overlap regions 1210 and 1208.

In an exemplary embodiment of the invention, the laser scanning is discrete, e.g., with a spot moving time shorter than 20%, 10% of the spot dwell time. In this case, overlap is defined between adjacent spots in row and between rows. If the scanning is continuous, overlap is mainly meaningful between rows. As noted above, overlap may have a reduced meaning when the time between successive heating events of a same spot is long enough to allow most of the heat to dissipate. In addition, the beam shape (generally non-uniform energy distribution) affects the actual amount of overlap. Thus, overlap regions 1204, 1208 and 1210 may not experience significant synergistic effects. Optionally, however, the scan settings are selected to avoid too high energy deposition in any part of the sclera. In some cases, a portion of the sclera is not directly irradiated by laser but is close enough to one or two or more laser irradiations to become ablated.

Following is a short estimation of energy levels. For a spot size of 400 micron diameter, power level of 24 watts, dwell time of 300 microseconds and overlap of 30%, the energy applied at a shot is $\sim 7.5 \times 10^{-3}$ Joule. The energy density is about 6 Joule/sqr·cm. This amount is considered sufficient for ablation. This number is increased (e.g., but up to 30%-50% for some portions) if one considers the overlap and somewhat reduced if losses in the system are considered. It is noted that for some parts of the sclera the energy density is not uniform but may vary within a factor of, for example, 1.2, 1.5, 2 or other factors.

In an exemplary embodiment of the invention, at least some of the overlaps, for example, at least 30% or 50% of overlaps are overlapping in space but are not near in time, for example, allowing, between 1 and 300 milliseconds, for example, between 10 and 100 milliseconds between a first targeting and an overlapping targeting.

General

It should be noted that the above systems and methods may be used for parts of the sclera not only over the Schlemm's canal. It should be noted that some features, such as discovery of the SC, can be applied using non-laser techniques, such as a scalpel (although lasers may be safer and/or easier to use).

The above embodiments may be packaged in various manners, including, for example, modules, add-ons for an OM and as part of an OM. Optionally, software for controlling the LACS is provided with a component of the LACS, for example, the scanner. Optionally, the aiming beam of the CO2 laser is used to show the scan pattern exercised by the scanner.

It is expected that during the life of a patent maturing from this application many relevant lasers and scanners will be developed and the scope of the terms "laser" and "scanner" are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

EXAMPLES

Various embodiments and aspects of the present invention as delineated hereinabove and as claimed in the claims section below find experimental support in the following example.

Evaluation of the Safety and Effectiveness of the OT-134 System in $CO_2$ Laser Assisted Non-Penetrating Deep Sclerectomy. (Human Clinical Trials)

Methods: A prospective single-arm, non-randomized, multi-center study. The study was performed in accordance with the Declaration of Helsinki. All the subjects or their legal guardians agreed to sign a written informed consent prior to study participation.

The inclusion criteria were defined as follows: all subjects must be ≥18 years of age, with clinical documented diagnosis of Primary Open Angle Glaucoma (POAG) or Pseudo-Exfoliative Glaucoma (PEXFG) in both eyes. Diagnosis requires: glaucomatous optic neuropathy, Shaffer angle greater than grade 2 and visual field defect attributed to glaucoma. All subjects had an indication for primary filtration surgery due to the presence of ocular hypertension, defined as an intraocular pressure (IOP)≥21 mm Hg in the study eye, as measured in 3 consecutive visits over a 90 day period before enrollment, while on maximal tolerated hypotensive medications. The patients had to be phakic or pseudophakic in the operated eye with no associated ocular disorder or associated ocular diseases but cataract and no prior surgical or laser intervention in study eye but cataract surgery with clear corneal incision. The Best corrected visual acuity (BCVA) in the fellow eye had to be >20/200.

Exclusion criteria: Subjects with diagnosis of glaucoma other than POAG or PEXFG, or dilated pupil diameter of less than 2 mm were excluded from the study as well as subjects with known allergy to the study medications or severe systemic disease and disabling conditions.

The baseline evaluation of all subjects was conducted prior to the surgical procedure and included the following: demographic details, general medical history, and ophthalmic history. Glaucoma history was documented, including: family history, disease duration, anti-glaucoma treatments in the past (medications & interventions), IOP control and disease progression analysis according to visual fields and optic discs damage.

All subjects were examined and the pre-operative ocular status was documented, including: refraction and best corrected visual acuity (BCVA) as measured with ETDRS chart. Biomicroscopic examination was preformed and the average of 3 repeated IOP measurements, using a Goldman tonometer, was recorded. Further baseline evolution also included: a gonioscopic examination, an average of 3 repeated measurements of central corneal thickness. Fundus examination and optic disc evaluation were performed, with attention to: C/D ratio, disc notches, splinters hemorrhages and discs size. A threshold 24-2 Humphrey perimetry, within 2 weeks prior to surgery, and stereoscopic disc photography were recorded.

Safety Outcomes were Defined as Follows;

Overall incidence of intra-operative device related adverse events

Early post-operative device related adverse events (through Day 7);

Cumulative and persistent (present at 3 and 6 months) device related adverse events.

Performance Endpoints:

1. Qualified Success Rate at 3 months (Rate of patients with IOP<21 mmHg with or without glaucoma medications at 3 months).

2. Complete Success Rate at 3 months (Rate of patients with IOP<21 mmHg without glaucoma medications at 3 months).

3. Failure rate: The definition of failure in the study: IOP<5, IOP>21 mmHg, complete loss of vision or performance of additional glaucoma surgery except for goniopuncture and needling.

4. Incidence of intra-operative perforations (macro).

The surgical procedure: The surgery was preformed under local anesthesia. Following routine preparation of the eye for sterile surgical conditions, a fornix-based peritomy was performed at the superior limbus, and the Tenon's capsule was dissected to expose the sclera. A partial thickness (one-third to one-half) limbal-based scleral flap up to 5×5 mm was be dissected at the limbus into clear cornea. The scanning shape and area size were set and the laser beam was focused. The treated area on the patient was defined and verified with the red aiming diode laser. The laser power, mode, laser beam focus, scanner dwell time, overlap, and repeat delay were verified. The cornea was protected with a wet sponge. The laser beam was applied to the scleral wall in an area that included the Schlemm's Canal until the outer wall of the Schlemm's Canal was ablated. The charred tissue was wiped after ablation every 1-3 laser scans, scanning proceeded until percolation was achieved and percolation zone length measured at least 2.5 mm. Prior to flap suture, Healon 5 was applied beneath the repositioned flap and the scleral flap was repositioned and secured in place using 2 interrupted 10-0 nylon sutures. The conjunctiva was repositioned and secured in place using interrupted 10-0 nylon sutures. Careful hemostasis was performed during the entire procedure. Antibiotic and steroid ointment were applied and the eye will be closed with a patch and shield.

Follow up: All subjects were examined according to the following schedule: 24(±12) hours post-operatively, at week 1 and 3 (±3 days), at week 6 and 14 (±2 weeks), and 6 months (±2 weeks) after surgery.

Statistical Methods:

The following statistical tests were used in the analysis of the data presented in this study:

Descriptive statistics: continuous variables were summarized using the mean, median, standard error, minimum and maximum values. Categorical variables were summarized using frequency counts and percentages.

95% Confidence Interval was calculated for the mean IOP measurements.

95% Confidence Interval was calculated for the Rate of success as defined in the primary and secondary endpoints.

Paired T-test was applied for testing the statistical significance of the changes in IOP. All tests applied were two-tailed, and p value of 5% or less was considered statistically significant. The data was analyzed using the SAS® software (SAS Institute, Cary N.C.).

Results;

Thirty seven subjects were included in the study. The study includes a total of 37 subjects from 3 sites: Mexico (14 subjects), India (13 subjects) and Russia (10 subjects). Mean age 64.1. 24.3% had PEXFG while the remaining 75.7% had POAG. Mitomycin C was used in 26.5% of the patients.

One subject was lost to follow up 6 weeks post surgery. 1 subject passed away due to Diabetes Mellitus complications 4 weeks post surgery. 1 subject was retrospectively excluded from the analysis of the results as he underwent YAG laser iridotomy pre-operatively.

3 patients were converted into standard trabeculectomy during the initial procedure due to protocol deviation as the initial scanning are failed to reach the area of Schlemm's canal. One subject underwent tube shunt surgery 4 weeks after the initial procedure as his IOP was uncontrolled. This patient was related as a failure and his intra-ocular pressures and hypotensive medications were analyzed up to tube implantation point.

The Results of the Remaining 30 Patients were Analyzed as Follows:

Schlemm's canal was easily recognized and treated in all 30 subjects.

Adequate percolation was achieved in all cases.

Figure 13:
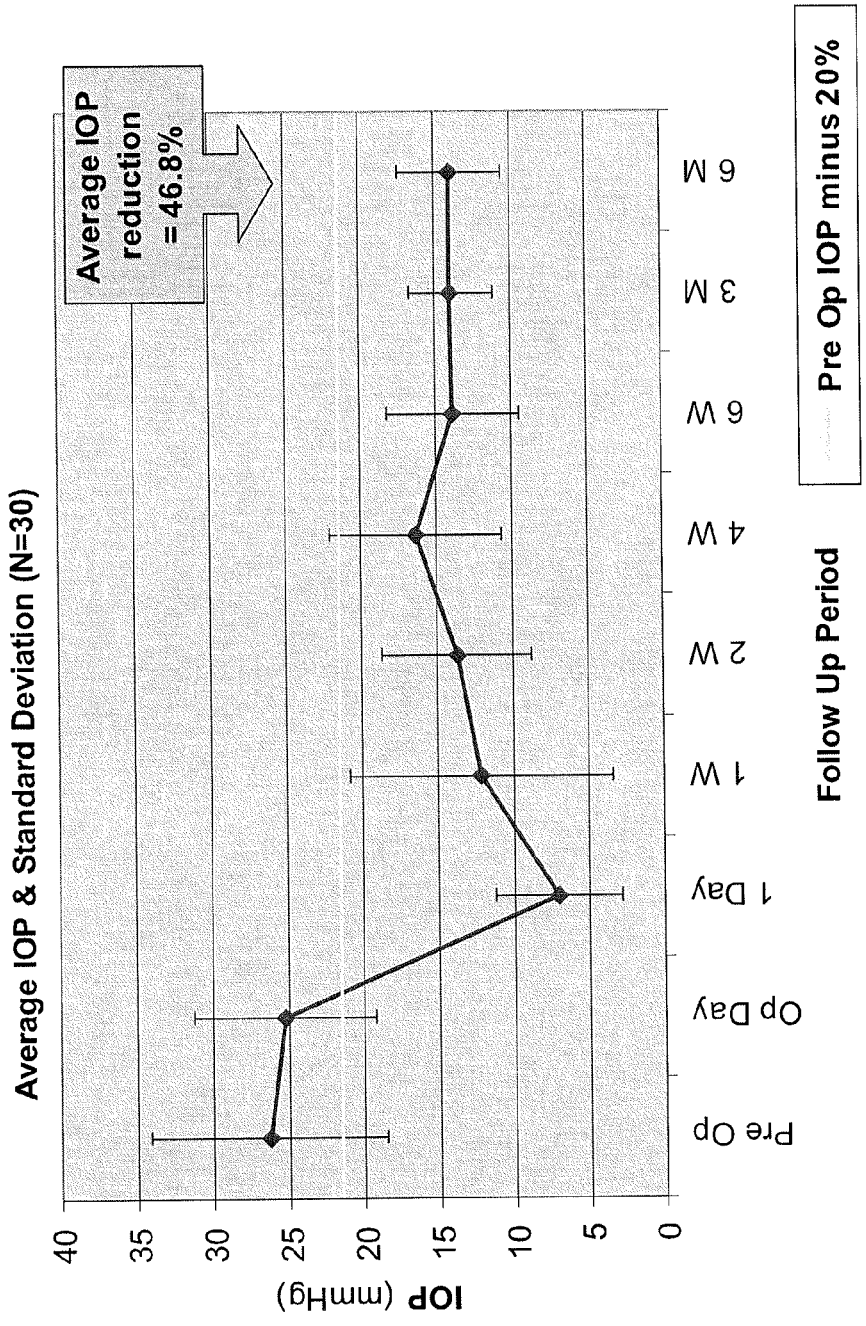
FIG. 13 is a chart showing reduction in intra-ocular pressure in patients treated in accordance with an exemplary embodiment of the invention.

The average pre-op IOP was 26.16 mmHg (median 24.00 mmHg) as compared to an average IOP of 14 mmHg (median 14.00 mmHg) at 6 months (p<0.001). The average IOP reduction was 44.05%. (FIG. 13)

Figure 16:
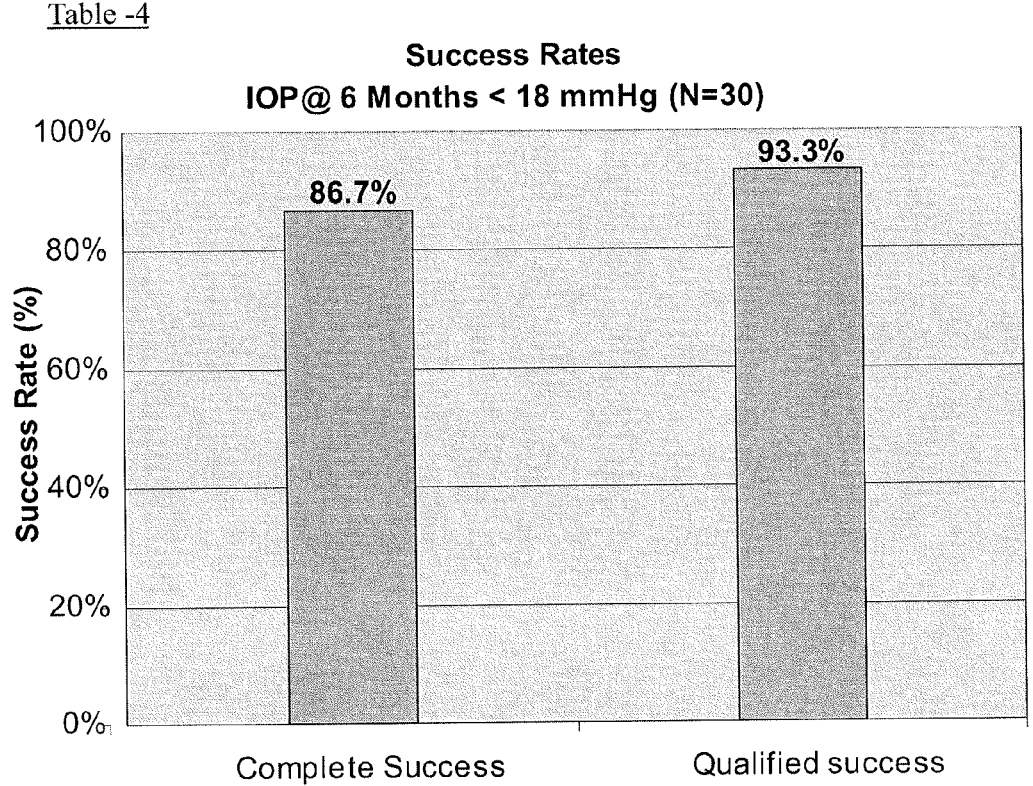
FIG. 16 is a chart showing complete and qualified success rates for patients treated in accordance with an exemplary embodiment of the invention.

The complete success rate was 86.7% at 6 months (IOP<18 mmHg without hypotensive medications). (FIG. 16)

The qualified success rate was 93.3% at 6 months (IOP<18 mmHg with and without hypotensive medications). (FIG. 16)

Figure 14:
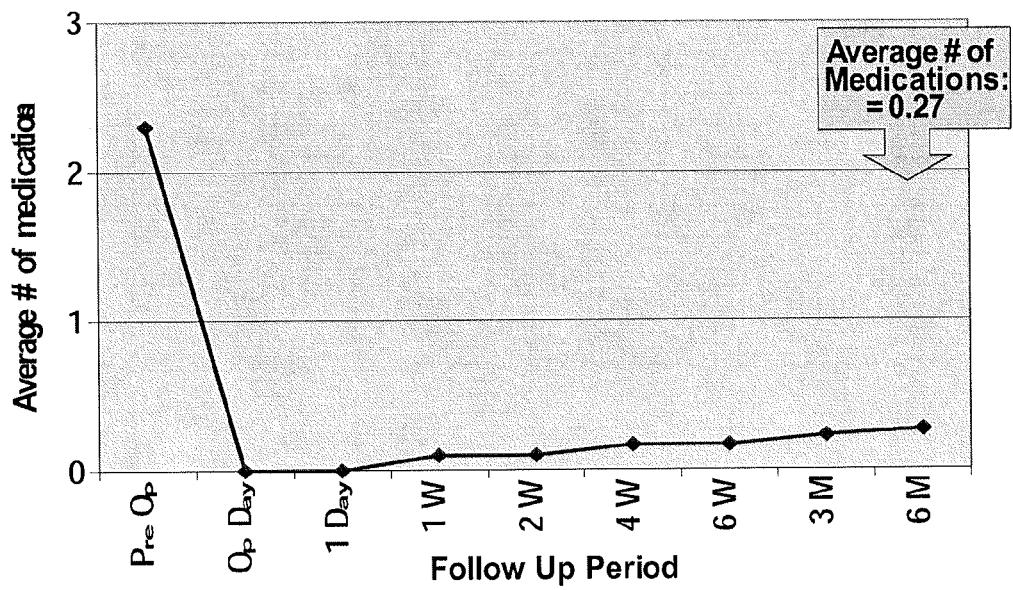
FIG. 14 is a chart showing reduction in drug usage in patients treated in accordance with an exemplary embodiment of the invention.

3 subjects were considered as failure: 1 underwent tube shunt procedure 4 weeks after the initial procedure due to uncontrolled IOP and the other two subjects had IOP>21 mmHg The average number of pre-operative hypotensive medications per patient was 2.3 as compared to 0.27 hypotensive medications per patient at 6 months (p<0.001). —(FIG. 14)

Figure 15:
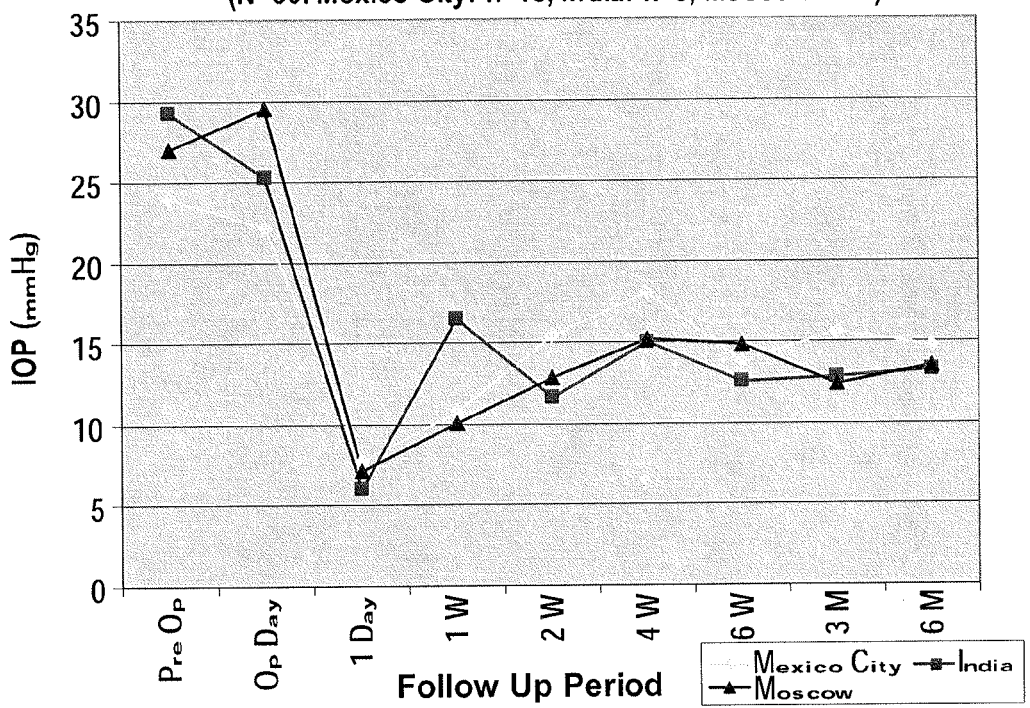
FIG. 15 is a chart showing a comparison between different sites at different geographical locations and different surgeons where patients were treated in accordance with an exemplary embodiment of the invention.

FIG. 15 shows the IOP results in the different sites. The similarity of the three graphs demonstrates the reproducibility of the results.

Post Operative Procedures:

Seven needling procedures were preformed in 6 subjects. One needling procedure was preformed 1 week after surgery, two were preformed 2 weeks post-surgery and 4 were preformed 6 weeks post initial procedure Two goniopuncture procedures were performed (2 and 4 weeks after the initial procedure).

One laser suture lysis was preformed 1 week post initial surgery.

No serious adverse events were recorded. No intra-operative device related adverse events were recorded. There were no intra-operative device technical issues operating the CO2 laser system. There were no cases of vision loss or of infection.

Documented adverse events: Mild-moderate peripheral anterior synechia (PAS) was recorded in 3 subjects and required no treatment.

Mild-moderate early post operative wound leak was inspected in 2 cases. Both resolved with conservative treatment (bandage contact lens).

One case of mild hyphema was recorded in one subject and was spontaneously absorbed.

Three cases of mild corneal complications were documented (1 mild dellen, and 2 superficial erosions). All three resolved with conservative treatment.

Conclusions:

The above experiments support the conclusion that CO2 laser assisted non penetrating deep sclerectomy is a highly effective, safe and relatively simple surgical procedure for lowering and control of the IOP in glaucoma and other patients. Laboratory studies and clinical experience exhibit a high safety profile and very promising mid-term clinical results.

The good results at 6 months follow up, the safety profile and the simple procedure are very relevant to all glaucoma patients and should be considered as an option of a first line procedure for patients with elevated IOP.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A laser control system, comprising:
   a scanner housing, wherein the scanner housing comprises:
      a focusing lens;
      at least two light sources disposed symmetrically with respect to an optical axis of the focusing lens, wherein the at least two light sources generate two converging beams toward a focal plane of the focusing lens;
      a beam reflecting element positioned on the optical axis and on a first side of the focusing lens; and
      a laser port at one end of the scanner housing, wherein the laser port is positioned on the optical axis and on the first side of the focusing lens; and
   a ring-shaped frame having an opening side coupled to the scanner housing on a second side of the focusing lens, wherein the ring-shaped frame comprises:
      a folding mirror mounted at the opening side of the ring-shaped frame, wherein the folding mirror is configured to control a direction of the two converging beams;
      at least one mechanism;
         wherein the at least one mechanism is operatively connected to the folding mirror;
         wherein the at least one mechanism is configured to adjust a position and an orientation of the folding mirror;
      a plurality of protrusions disposed on the ring-shaped frame;
         wherein the plurality of protrusions are operatively connected to an adaptor which couples the ring-shaped frame with a microscope; and
      wherein the plurality of protrusions are configured to adjust a position and a rotation of the ring-shaped frame relative to the microscope; and
      wherein the plurality of protrusions comprise:
         at least one first protrusion configured to lock the ring-shaped frame to the adapter, and
         at least one second protrusion configured to allow the rotation of the ring-shaped frame around an axis of the microscope and lock a rotation position of the ring-shaped frame.

2. The system of claim 1, wherein the beam reflecting element comprises two perpendicular mirrors, each of the two perpendicular mirrors mounted on an actuator.

3. The system of claim 2, wherein the actuators are driven by electronic signals creating a scanner pattern.

4. The system of claim 1, wherein the laser port is configured to receive input from an ablation laser.

5. The system of claim 1, wherein the scanner housing further includes a displacement element detachably coupled to the focusing lens, the displacement element configured to control a distance between the focusing lens and the folding mirror.

6. The system of claim 5, wherein the displacement element further comprises a micrometer moving the focusing lens towards or away from the folding mirror along the optical axis adjusting the focal location of the focusing lens.

7. The system of claim 1, wherein the folding mirror is configured to be transparent to most wavelengths of visible light and configured to reflect both ablation wavelengths and patterned light.

8. The system of claim 1, wherein the plurality of protrusions are configured to positioned at points on the ring-shaped ring defining a geometric shape symmetric with respect to the optical axis of the focusing lens, and the symmetric geometric shape has a minimum diameter smaller than that of a lip of the adaptor.

* * * * *